(12) United States Patent
Jermy et al.

(10) Patent No.: US 11,207,348 B2
(45) Date of Patent: Dec. 28, 2021

(54) SPINEL FERRITE IMPREGNATED MESOPOROUS SILICA CONTAINING A PLATINUM COMPLEX

(71) Applicant: Imam Abdulrahman Bin Faisal University, Dammam (SA)

(72) Inventors: B. Rabindran Jermy, Dammam (SA); Vijaya Ravinayagam, Dammam (SA); Abdulhadi Baykal, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

(21) Appl. No.: 16/394,543

(22) Filed: Apr. 25, 2019

(65) Prior Publication Data
US 2020/0338122 A1  Oct. 29, 2020

(51) Int. Cl.
*A61K 33/243* (2019.01)
*A61K 47/02* (2006.01)
*A61P 35/00* (2006.01)
*A61K 47/14* (2017.01)
*B82Y 5/00* (2011.01)

(52) U.S. Cl.
CPC ............ *A61K 33/243* (2019.01); *A61K 47/02* (2013.01); *A61P 35/00* (2018.01); *A61K 47/14* (2013.01); *B82Y 5/00* (2013.01)

(58) Field of Classification Search
None
See application file for complete search history.

(56) References Cited

U.S. PATENT DOCUMENTS

| 2010/0056360 A1 | 3/2010 | Lee |
| 2014/0186268 A1* | 7/2014 | Vasiljeva ............... C01G 49/08 |
| | | 424/9.321 |

(Continued)

FOREIGN PATENT DOCUMENTS

| CN | 103464093 A | 12/2013 |
| KR | 10-2007-0068871 | 7/2007 |
| KR | 102500296 A | 6/2012 |

OTHER PUBLICATIONS

Mesoporous silica SBA-16 sold by Sigma-Aldrich ([retrieved from on-line website: https://www.sigmaaldrich.com/US/en/product/aldrich/806927, last visit Jun. 23, 2021]) (Year: 2021).*

(Continued)

*Primary Examiner* — Kyung S Chang
(74) *Attorney, Agent, or Firm* — Oblon, McClelland, Maier & Neustadt, L.L.P.

(57) ABSTRACT

A nanotherapeutic having platinum complexes encapsulated by a nanoformulation containing at least one spinel ferrite of formula $CuFe_2O_4$, $NiFe_2O_4$, $CoFe_2O_4$, and $MnFe_2O_4$ deposited on mesoporous silica. A method of preparing the nanotherapeutic that involves mixing a metal(II) salt and a Fe(III) salt with the mesoporous silica nanoparticles to form a powdery mixture, calcining the powdery mixture to form the nanoformulation, and mixing the nanoformulation with the platinum complex. A method for treating cancer with the nanotherapeutic.

4 Claims, 13 Drawing Sheets

(56) References Cited

U.S. PATENT DOCUMENTS

2014/0212479 A1* 7/2014 Zeinelden .............. A61K 9/127
424/450
2020/0038525 A1* 2/2020 Jermy ................ A61K 47/6923

OTHER PUBLICATIONS

Surowiec, et al. ; Influence of annealing temperature on structural and magnetic properties of MnFe2O4 nanoparticles ; NUKLEONIKA 60(1); pp. 137-141 ; 2015 ; 5 Pages.

Sahoo, et al. ; Biocompatible mesoporous silica-coated superparamagnetic manganese ferrite nanoparticles for targeted drug delivery and MR imaging applications ; Journal of Colloid and Interface Science, vol. 431 ; pp. 31-41 ; Oct. 1, 2014 ; 3 Pages ; Abstract Only.

Berger, et al. ; Properties of mesostructured silica coated CoFe2O4 versus Fe3O4-silica composites ; Journal of Alloys and Compounds 708 C ; pp. 278-284 ; 2017 ; 2 Pages ; Abstract Only.

Chen, et al. ; Preparation and Characterization of Magnetic Cobalt Ferrites/SBA-15 Nanocomposite Adsorbents and the Removal of Methylene Blue ; Nano vol. 12, No. 5 ; 2017 ; 3 Pages ; Abstract Only.

* cited by examiner

| Drug Group | Equation | EC50 value (mg/ml) |
|---|---|---|
| A | $y = 74.383e^{2.6587x}$ | -0.14940 |
| B | $y = 78.482e^{-0.128x}$ | 3.52224 |
| C | $y = 94.143e^{0.157x}$ | -0.40305 |
| D | $y = 52.635e^{-100.6x}$ | 0.00051 |
| E | $y = 66.146e^{-1.547x}$ | 0.18089 |
| F | $y = 87.981e^{-0.206x}$ | 2.74319 |

SPINEL FERRITE IMPREGNATED MESOPOROUS SILICA CONTAINING A PLATINUM COMPLEX

STATEMENT OF FUNDING ACKNOWLEDGEMENT

This project was funded by Deanship of Scientific Research (DSR), Imam Abdulrahman Bin Faisal University (IAU) under grant numbers 2016-099-IRMC and 2016-072-DSR.

BACKGROUND OF THE INVENTION

Technical Field

The present disclosure relates to a nanotherapeutic involving a spinel ferrite impregnated mesoporous silica loaded with an anti-proliferative platinum complex. A method of preparing the nanotherapeutic, and a method of treating cancer using the nanotherapeutic are also disclosed.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Cancer burden is expected to rise to 24 million in 2035 globally. The continuing advancement of nanotechnology has increased chances to cure chronic cancer, diabetes, and other metabolic disorders. Using nanoparticles for targeted drug delivery, bioimaging, bioengineering, and stem cell applications may be a promising tactic for the treatment of cancer [F. ud Din, W. Aman, I. Ullah, O. S. Qureshi, O. Mustapha, S. Shafique, A. Zeb, Effective use of nanocarriers as drug delivery systems for the treatment of selected tumors, Int J Nanomedicine 12 (2017) 7291-7309]. An important feature of nanotherapeutics is the ability to accommodate multiple components into a single nanostructure that exhibits a variety of functions. However, challenges including low bioavailability (about 5-10%), burst release, and low targeting accuracy need to be addressed in order to develop an effective nano drug delivery system.

Multifunctional theranostic nanoparticles with imaging contrast agents have attracted much attention in recent years. Magnetic nanosilica drug carrier capable of responding to external magnetic field may assist in bioimaging (magnetic resonance imaging), magnetically targeted drug delivery, enzyme lysozyme immobilization, hyperthermia, and tissue repairs. Magnetic nanosilica has shown the potential to be loaded with commercial cancer drugs.

In particular, superparamagnetic iron oxide nanoparticles (SPIONs) with intrinsic magnetic characteristics have been approved by FDA (U.S. food and drug administration) for clinical uses [G. Jarockyte, E. Daugelaite, M. Stasys, U. Statkute, V. Poderys, T-C. Tseng, S-H. Hsu, V. Karabanovas, R. Rotomskis, Accumulation and Toxicity of Superparamagnetic Iron Oxide Nanoparticles in Cells and Experimental Animals, Int J Mol Sci. 17 (2016) 1193]. Mesoporous silica (e.g. SBA-15 (p6 mm)) containing magnetic $Fe_3O_4$ has been reported to be effective for drug adsorption and delivery [Z. Vargas-Osorio, M. A. Gonzalez-Gomez, Y. Pineiro, C. Vazquez-Vazquez, C. Rodriguez-Abreu, M. A. Lopez-Quintela, J. Rivas, Novel synthetic routes of large-pore magnetic mesoporous nanocomposites (SBA-15/$Fe_3O_4$) as potential multifunctional theranostic nanodevices, J. Mater. Chem. B 5 (2017) 9395]. A biodegradable silica/iron oxide nanocomposite with mesopores ranging from 20-60 nm was reported for protein Ferritin delivery (cargo size>15 nm) [Omar H, Croissant J G, Alamoudi K, Alsaiari S, Alradwan I, Majrashi M A (2017) Biodegradable Magnetic Silica@Iron Oxide Nanovectors with Ultra-Large Mesopores for High Protein Loading, Magnetothermal Release, and Delivery. J. Control. Release 259, 187-194]. However, SPIONs/silica based nanostructures often have low saturation magnetization values. For instance, silica/iron oxide nanocomposite only showed a magnetization value of 1.65 emu/g based on magnetometer (SQUID) analysis.

A recent study has demonstrated that loading SPIONs (10 wt %) onto silica particles with various structures could induce different levels of magnetization. For example, SPIONs loaded micron-sized spherical silica exhibited a highest magnetization value of 1.44 emu/g, while SPIONs loaded silicalite particles showed a lowest value of 0.08 emu/g [B. R. Jermy, V. Ravinayagam, S. Akhtar, W. A. Alamoudi, N. A. Alhamed, A. Baykal. Magnetic Mesocellular Foam Functionalized by Curcumin for Potential Multifunctional Therapeutics, J Supercond Nov Magn (2018). https://doi.org/10.1007/s10948-018-4921-3]. Such variation could be attributed to the presence of large surface area of silica that tends to convert SPIONs into nano-sized particles (3-21 nm) rather than crystalline oxides. In general, a large magnetization value is required for a nanoformulation to perform multiple tasks effectively. Magnetization is expected to increase by loading a larger amount of SPIONs onto the nanoformulation. However, a large loading of SPIONs could lead to formation of mixtures of iron oxide species ($\alpha$-$Fe_2O_3$, $Fe_3O_4$ and $\gamma$-$Fe_2O_3$).

Spinel ferrites may be formed by modifying the surface of iron oxide with transition heteroatoms (M). Magnetic nanoferrites are inexpensive and can be easily prepared without multistep protocols. Ferromagnetism may occur when anti parallel spins of $Fe^{3+}$ are present at tetrahedral sites, and transition heteroatoms ($M^{2+}$) occupy octahedral sites. Recently, a low-cost preparation of nano copper ferrite using citrate sol gel technique was reported [Md. Amir, H. Gungunes, Y. Silmani, N. Tashkandi, H. S. El Sayed, F. Aldakheel, M. Sertkol, H. Sozeri, A. Manikandan, I. Ercan, A. Baykal, Journal of Superconductivity and Novel Magnetism, https://doi.org/10.1007/s10948-018-4733-5]. In addition, several metal-based ferrite systems have been reported lately for biomedical applications such as hyperthermia, magnetic resonance imaging, and drug delivery [M. R. Phadatare, V. M. Khot, A. B. Salunkhe, N. D. Thorat, S. H. Pawar, Studies on polyethylene glycol coating on $NiFe_2O_4$ nanoparticles for biomedical applications, Journal of Magnetism and Magnetic Materials, 324 (2012) 770-772; and I. Sharifi, H. Shokrollahi, S. Amiri, Ferrite-based magnetic nanofluids used in hyperthermia applications, Journal of Magnetism and Magnetic Materials 324 (2012) 903-915, each incorporated herein by reference in their entirety].

However, spinel ferrite nanoparticles tend to form aggregations due to strong magnetic dipole-dipole interactions. Silica- and carbon-based supports were used to reduce the aggregation. Notably, different types of nanocomposite having Co-, Ni-, Mn- and Fe-based ferrites deposited over mesoporous carbon capsules as supports were reported by Fuertes et al. [A. B. Fuertes, T. Valdes-Solis, M. Sevilla, Fabrication of Monodisperse Mesoporous Carbon Capsules Decorated with Ferrite Nanoparticles, *J. Phys. Chem. C*

2008, 112, 3648-3654, incorporated herein by reference in its entirety]. Carbon capsule supports with a shell thickness of about 50 nm demonstrated a high loading capacity of ferrites at about 30-50 wt %. Ferrites with a particle size between 9-17 nm were observed at external carbon layers.

The magnetic properties of $ZnFe_2O_4$/MCM-41 and $NiFe_2O_4$/MCM-41 synthesized through wet impregnation technique have been studied and compared with bare ferrites. The findings showed that ferrites enclosed inside the non-magnetic hexagonal pores of MCM-41 exhibited smaller dipolar interactions and reduced magnetization value due to surface anisotropy effect [M. Virumbrales, R. Saez-Puche, M. José Torralvo, V. Blanco-Gutierrez, Mesoporous Silica Matrix as a Tool for Minimizing Dipolar Interactions in $NiFe_2O_4$ and $ZnFe_2O_4$ Nanoparticles, Nanomaterials 2017, 7, 151, incorporated herein by reference in its entirety].

Bullita et al. [S. Bullita, A. Casu, M. F. Casula, G. Concas F. Congiu, A. Corrias A. Falqui, D. Loche and C. Marras, $ZnFe_2O_4$ nanoparticles dispersed in a highly porous silica aerogel matrix: a magnetic study, Phys. Chem. Chem. Phys., 2014, 16, 4843, incorporated herein by reference in its entirety] reported the superparamagnetic effect of a zinc ferrite system over aerogel. The effect of calcination of zinc ferrite/aerogel nanocomposite at different temperatures between 450-900° C. in static air (450° C. for 1 h, 750° C. for 1 h and 6 h, 900° C. for 1 h) was studied. It was found that the thermal treatment temperature might directly impact the particle size of $ZnFe_2O_4$, as well as the inversion degree of normal bulk spinel ferrite. Mesoporous $Cu_{1-x}Zn_xFe_2O_4$ system has been reported using nanocasting technique [N. Najmoddin, A. Beitollahi, H. Kavas, S. M. Mohseni, H. Rezaie, J. Åkerman, M. S. Toprak, XRD cation distribution and magnetic properties of mesoporous Zn-substituted $CuFe_2O_4$, Ceramics International 40 (2014) 3619-3625, incorporated herein by reference in its entirety]. Based on Bertaut analysis, doping of Zn tends to form mixed inverse spinels where Zn occupies the A site, while Cu prefers to occupy the B site. SQUID-VSM analysis observed superparamagnetic behavior of the mixed metal oxide spinel composite. Temperature dependence study using field cooling and zero field cooling analysis (ZFC/FC) showed spin glass like surface layers in the mixed metal oxide spinel composite. $CuFe_2O_4$ and activated carbon composite prepared using co-precipitation technique was reported by [G. Zhang, J. Qu, H. Liu, A. T. Cooper, R. Wu, $CuFe_2O_4$/ activated carbon composite: A novel magnetic adsorbent for the removal of acid orange II and catalytic regeneration, Chemosphere 68 (2007) 1058-1066, incorporated herein by reference in its entirety]. The study showed that the presence of spinel over carbon support was useful for adsorption and had minimal impact on the surface area occupation and pore size distribution. Hammiche-Bellal et al. [Y. Hammiche-Bellal, N. Zouaoui-Mahzoul, I. Lounas, A. Benadda, R. Benrabaa, A. Auroux, L. Meddour-Boukhobza, A. Djadoun, Cobalt and cobalt-iron spinel oxides as bulk and silica supported catalysts in the ethanol combustion reaction, Journal of Molecular Catalysis A: Chemical 426 (2017) 97-106, incorporated herein by reference in its entirety] studied the effect of cobalt and cobalt ferrite on silica and bulk support through impregnation and co-precipitation techniques. Mixed metal oxides of spinels showed highly active sites and a uniform dispersion was found on the silica surface rather than bulk surface.

Briefly, the synthesis and characterization of Cu, Ni, Co and Mn spinel ferrites have been carried out. However, nanoformulations having Cu, Ni, Co and Mn spinel ferrites deposited on monodispersed hydrophilic silica (HYPS) for drug adsorption and delivery has not been explored. Furthermore, studies regarding adsorption, releasing, and toxicity of cancer drug (e.g. cisplatin) loaded spinel ferrite/ monodispersed hydrophilic has not been conducted.

In view of the forgoing, one objective of the present disclosure is to provide a nanotherapeutic involving a platinum complex loaded nanoformulation that contains a spinel ferrite (e.g. $CuFe_2O_4$, $NiFe_2O_4$, $CoFe_2O_4$, $MnFe_2O_4$) impregnated mesoporous silica. A further objective of the present disclosure is to provide a method of making the nanotherapeutic and a method of treating cancer by administrating the nanotherapeutic. The nanotherapeutic demonstrates magnetic activity and exhibit efficient loading and releasing capability of platinum complexes with anticancer efficacy.

BRIEF SUMMARY OF THE INVENTION

According to a first aspect, the present disclosure relates to a nanotherapeutic involving i) a nanoformulation that contains mesoporous silica nanoparticles and a spinel ferrite of formula (I)

$$MFe_2O_4 \quad (I)$$

and ii) a platinum complex encapsulated within pores of the nanoformulation, wherein M is at least one transition metal element selected from the group consisting of Cu, Ni, Co, and Mn, the spinel ferrite is impregnated on the mesoporous silica nanoparticles, and the spinel ferrite is present in an amount of 15-50 wt % relative to a total weight of the nanoformulation.

In one embodiment, the spinel ferrite of formula (I) is $CuFe_2O_4$, $NiFe_2O_4$, or both.

In one embodiment, the pores of the nanoformulation have a pore diameter in a range of 10-25 nm.

In one embodiment, the nanoformulation has a pore volume in a range of 0.05-0.3 $cm^3$/g.

In one embodiment, the nanoformulation has a BET surface area in a range of 15-70 $m^2$/g, In one embodiment, the nanoformulation has a saturation magnetization value in a range of 1-18 emu/g.

In one embodiment, the platinum complex is present at a concentration of 0.01-10 mmol/g relative to a total weight of the nanoformulation.

In one embodiment, the platinum complex is at least one selected from the group consisting of cisplatin, carboplatin, oxaliplatin, nedaplatin, triplatin tetranitrate, phenanthriplatin, picoplatin, and satraplatin.

In one embodiment, the platinum complex is cisplatin.

In one embodiment, the nanotherapeutic further comprises one or more pharmaceutically acceptable carriers and/or excipients selected from the group consisting of a buffer, an inorganic salt, a fatty acid, a vegetable oil, a synthetic fatty ester, a surfactant, and a polymer.

According to a second aspect, the present disclosure relates to a method of preparing the nanotherapeutic of the first aspect. The method involves the steps of i) mixing an M(II) salt and a Fe(III) salt with the mesoporous silica nanoparticles to form a powdery mixture, ii) calcining the powdery mixture to form a nanoformulation, and iii) mixing the nanoformulation and a platinum complex in an aqueous solution, thereby forming the nanotherapeutic.

In one embodiment, the calcining is performed at a temperature of 600-1,000° C.

In one embodiment, the aqueous solution is saline.

In one embodiment, the platinum complex is present in the aqueous solution at a concentration of 0.1-30 g/L, and the nanoformulation is present in the aqueous solution at a concentration of 2-600 g/L, each relative to a total volume of the aqueous solution.

According to a third aspect, the present disclosure relates to a method for treating a proliferative disorder. The method involves administering the nanotherapeutic of the first aspect to a subject in need of therapy.

In one embodiment, 0.5-800 mg/kg of the nanotherapeutic is administered per body weight of the subject.

In one embodiment, the platinum complex is cisplatin.

In one embodiment, the proliferative disorder is a cancer selected from the group consisting of breast cancer, ovarian cancer, cervical cancer, testicular cancer, colon cancer, bladder cancer, and lung cancer.

In one embodiment, the cancer is breast cancer.

In one embodiment, the subject is a mammal.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
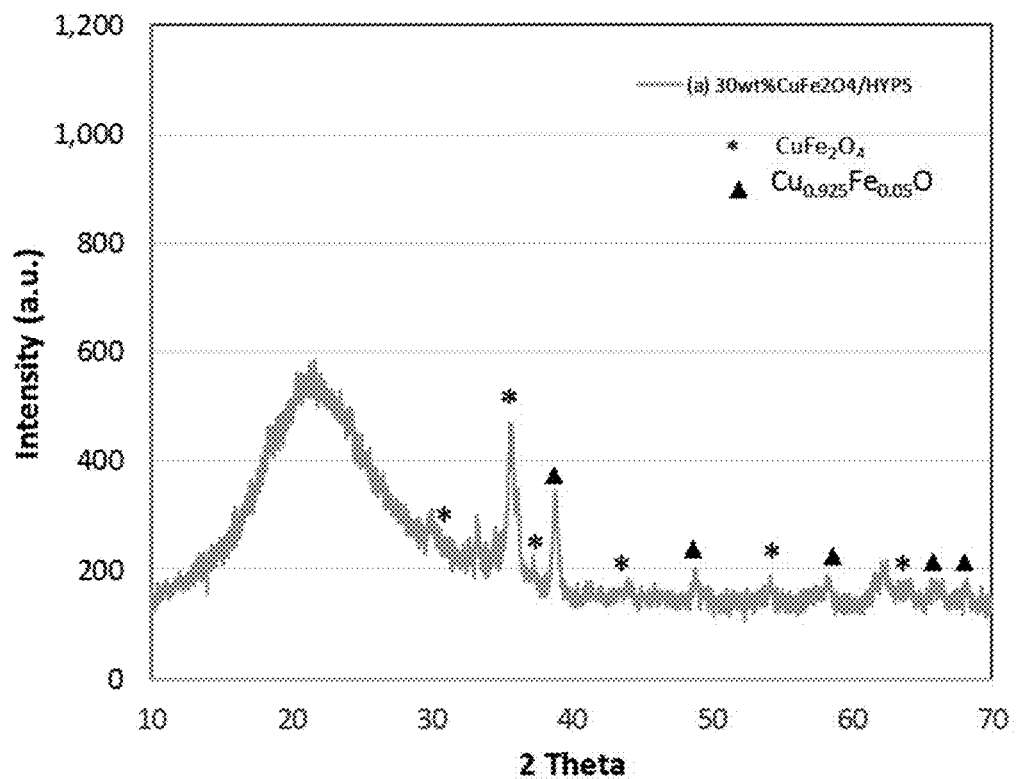
FIG. 1 shows X-ray diffraction (XRD) patterns of nanoformulation containing copper ferrite ($CuFe_2O_4$).

Embodiments of the present disclosure will now be described more fully hereinafter with reference to the accompanying drawings, in which some, but not all embodiments of the disclosure are shown.

The present disclosure will be better understood with reference to the following definitions. As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

As used herein, the terms "complex", "compound", and "product" are used interchangeably, and are intended to refer to a chemical entity, whether in the solid, liquid or gaseous phase, and whether in a crude mixture or purified and isolated.

The present disclosure includes all hydration states of a given salt or formula, unless otherwise noted. For example, copper(II) nitrate includes anhydrous $Cu(NO_3)_2$, monohydrate $Cu(NO_3)_2 \cdot H_2O$, hemi(pentahydrate) $Cu(NO_3)_2 \cdot 2.5H_2O$, trihydrate $Cu(NO_3)_2 \cdot 3H_2O$, and any other hydrated forms or mixtures. Iron(III) nitrate includes anhydrous $Fe(NO_3)_3$, and hydrated forms such as iron(III) nitrate nonahydrate $Fe(NO_3)_3 \cdot 9H_2O$.

The present disclosure is intended to include all isotopes of atoms occurring in the present compounds. Isotopes include those atoms having the same atomic number but different mass numbers. By way of general example, and without limitation, isotopes of hydrogen include deuterium and tritium, isotopes of carbon include $^{12}C$, $^{13}C$, and $^{14}C$, isotopes of oxygen include $^{16}O$, $^{17}O$, and $^{18}O$, isotopes of copper include $^{63}Cu$ and $^{65}Cu$, and isotopes of iron include $^{54}Fe$, $^{56}Fe$, $^{57}Fe$, and $^{58}Fe$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

According to a first aspect, the present disclosure relates to a nanotherapeutic involving i) a nanoformulation that contains mesoporous silica nanoparticles and a spinel ferrite of formula (I)

$$MFe_2O_4 \quad (I)$$

and ii) a platinum complex encapsulated within pores of the nanoformulation.

A "mesoporous support" refers to a porous support material with largest pore diameters ranging from about 2-50 nm, preferably 3-45 nm, preferably 4-40 nm, preferably 5-25 nm. As used herein, "mesoporous silica" refers to a mesoporous support comprising silica ($SiO_2$). Non-limiting examples of mesoporous silica include MCM-48, MCM-41, MCM-18, SBA-15, and SBA-16.

A particle is defined as a small object that behaves as a whole unit with respect to its transport and properties. An average diameter (e.g., average particle size) of the particle, as used herein, and unless otherwise specifically noted, refers to the average linear distance measured from one point on the particle through the center of the particle to a point directly across from it. For a circle, an oval, an ellipse, and a multilobe, the term "diameter" refers to the greatest possible distance measured from one point on the shape through the center of the shape to a point directly across from it. For polygonal shapes, the term "diameter", as used herein, and unless otherwise specified, refers to the greatest possible distance measured from a vertex of a polygon through the center of the face to the vertex on the opposite side. The mesoporous silica support used herein may be in the form of particles (i.e. mesoporous silica particles). In one embodiment, the mesoporous silica particles have an average particle size of 0.01-3 µm, 0.05-2 µm, 0.1-1 µm, or 0.2-0.5 µm.

Nanoparticles are particles between 1 and 100 nm in size. In preferred embodiments, the mesoporous silica support of the present disclosure is present in the form of nanoparticles. In a preferred embodiment, the mesoporous silica nanoparticles have an average particle size of 10-100 nm, 25-95 nm, 30-90 nm, 40-85 nm, 50-85 nm, 60-80 nm, or 70-75 nm. The mesoporous silica nanoparticles may preferably be spherical or substantially spherical (e.g., oval or oblong shape). In other embodiments, the mesoporous silica nanoparticles can be of any shape that provides desired permeability and/or stability of the nanoformulation, and/or release rates of encapsulated compounds (e.g., the platinum complex). For example, the mesoporous silica nanoparticles may be in a form of at least one shape such as a sphere, a rod, a pentagon, a hexagon, a prism, a disc, and a platelet.

Dispersity is a measure of the heterogeneity of sizes of particles in a mixture. In probability theory and statistics, the coefficient of variation (CV) also known as relative standard deviation (RSD) is a standardized measure of dispersion of a probability distribution. It is expressed as a percentage and is defined as the ratio of the standard deviation (σ) of to the mean (µ, or its absolute value |µ|). The CV or RSD is widely used to express precision and repeatability. It shows the extent of variability in relation to the mean of a population. Preferably, the mesoporous silica nanoparticles have a narrow size dispersion, i.e. monodispersity. As used herein, "monodisperse", "monodispersed" and/or "monodispersity" refers to nanocapsules having a CV or RSD of less than 25%, preferably less than 20%.

The mesoporous silica nanoparticles may be monodisperse with a coefficient of variation or relative standard deviation (ratio of the particle size standard deviation to the particle size mean) of less than 15%, less than 12%, less than 10%, less than 9%, less than 8%, less than 7%, less than 6%, less than 5%, or preferably less than 2%. In one embodiment, the mesoporous silica nanoparticles are monodisperse and have a particle diameter distribution in a range of 75% of the average particle diameter to 125% of the average particle diameter, 80-120%, 85-115%, 86-114%, 87-113%, 88-112%, 89-111%, 90-110%, or preferably 95-105% of the average particle diameter. Alternatively, the mesoporous silica nanoparticles are polydisperse with a coefficient of variation or relative standard deviation (ratio of the particle size standard deviation to the particle size mean) of more than 15%, 20%, or 30%. The polydisperse nanoparticles may have a particle diameter distribution in a range of 25% of the average particle diameter to 175% of the average particle diameter, 30-160%, or 50-150% of the average particle diameter.

The silica nanoparticles may be agglomerated or non-agglomerated (i.e., the nanoparticle are well separated from one another and do not form clusters). In some embodiments, the silica nanoparticles may cluster and form agglomerates having an average diameter in a range of 2-50 µm, 4-25 µm, or 5-10 µm.

The Brunauer-Emmet-Teller (BET) theory (S. Brunauer, P. H. Emmett, E. Teller, *J. Am. Chem. Soc.* 1938, 60, 309-319, incorporated herein by reference) aims to explain the physical adsorption of gas molecules on a solid surface and serves as the basis for an important analysis technique for the measurement of a specific surface area of a material. Specific surface area is a property of solids which is the total surface area of a material per unit of mass, solid or bulk volume, or cross sectional area. The surface area and pore size distribution may be characterized using a method developed by Barrett, Joyner and Halenda (BJH) (E. P. Barrett, L. G. Joyner, P. P. Halenda, *J. Am. Chem. Soc.* 1951, 73, 373-380, incorporated herein by reference) through gas adsorption analysis. In preferred embodiments, pore volume and BET surface area are measured by gas adsorption analysis, preferably $N_2$ adsorption analysis.

In one or more embodiments, the mesoporous silica nanoparticles have a pore volume of 0.2-0.5 $cm^3$/g, 0.3-0.45 cm³/g, 0.32-0.4 cm³/g, or about 0.35 cm³/g. In one related embodiment, the mesoporous silica nanoparticles have a pore diameter of 2-10 nm, 4-9 nm, 5-8.5 nm, or about 8.3 nm. In another related embodiment, the mesoporous silica nanoparticles have a BET surface area of 80-400 m²/g, 100-300 m²/g, 120-250 m²/g, 150-200 m²/g, or about 170 m²/g.

In certain embodiments, the mesoporous silica support used herein has pore channels that are regularly arranged. For example, the mesoporous silica support may be in the form of a honeycomb-like structure having pore channels parallel or substantially parallel to each other within a two-dimensional hexagon (e.g. SBA-15, MCM-41). Alternatively, other mesoporous silica structures such as SBA-11 having a cubic structure, SBA-12 having a three-dimensional hexagonal structure, and SBA-16 having a cubic in cage-like structure may be used as the mesoporous silica support. The mesoporous silica nanoparticles may be available from commercial vendors including, without limitation, Superior Silica, Sigma Aldrich, and Alfa Aesar.

As defined herein, a spinel is a metal oxide compound with a general formula $A^{2+}B_2^{3+}O_4^{2-}$, where "A" and "B" are metal ions. In one embodiment, "A" may be Zn, Cu, Co, Mn, Ni, Mg, Be, and/or Ti, and "B" may be Al, Fe, Cr, and/or V. Preferably, spinel compounds are in the form of crystals, with the oxide anions arranged in a cubic close-packed lattice, and with the metal ions occupying octahedral and/or tetrahedral sites within the lattice. Preferably, the $A^{2+}$ metal ions occupy the tetrahedral sites, and the $B^{3+}$ metal ions occupy the octahedral sites, though there may be instances where the metal ions are switched. The $A^{2+}$ and $B^{3+}$ metal ions may occupy sites in the lattice at regular spacings or may be distributed randomly.

A spinel ferrite is defined herein as an iron-containing spinel compound with a formula (I)

$$MFe_2O_4 \quad (I)$$

where "M" is a metal ion. In one embodiment, "M" may be Zn, Cu, Co, Mn, Ni, Mg, Be, and/or Ti. In a preferred embodiment, M is at least one transition metal element selected from the group consisting of Cu, Ni, Co, and Mn. Most preferably, the spinel ferrite of formula (I) is $CuFe_2O_4$, $NiFe_2O_4$, or both.

In certain embodiments, the spinel ferrite of the present disclosure is a mixed spinel ferrite with a formula $M_x^{2+}N_{(1-x)}^{2+}Fe_2O_4$, where "M" is the same as previously described, and "N" may be a metal ion (e.g. Zn, Cu, Co, Mn, Ni, Mg, Be, Ti) that is different from 'M', and x is greater than 0 and smaller than 1. Atomic ratios of the mixed spinel ferrites may be determined by elemental analysis techniques such as energy-dispersive X-ray spectroscopy (EDX), X-ray photoelectron spectroscopy (XPS), inductively coupled plasma mass spectrometry (ICP-MS), and neutron activation analysis.

In preferred embodiments, the spinel ferrite disclosed herein is copper ferrite $CuFe_2O_4$, nickel ferrite ($NiFe_2O_4$), a mixed spinel ferrite having oxygen atoms and metal atoms including copper and nickel (i.e. $Cu_xNi_{(1-x)}Fe_2O_4$, where 0<x<1), or a mixture thereof. In at least one embodiment, the spinel ferrite is devoid of other metal atoms such as cobalt (Co) and manganese (Mn).

The nanoformulation of the present disclosure comprises the aforementioned spinel ferrite impregnated on the mesoporous silica nanoparticles. As used herein, "impregnated" or "disposed on" describes being partially filled throughout, saturated, permeated, and/or infused. The spinel ferrite may be affixed on one or more surfaces of the mesoporous silica nanoparticles. For example, the spinel ferrite may be affixed on an outer surface of the mesoporous silica nanoparticles, or within pore spaces of the mesoporous silica nanoparticles. Preferably, the spinel ferrite is affixed to external pores of the mesoporous silica nanoparticles. The spinel ferrite may be affixed to the mesoporous silica nanoparticles in any reasonable manner, such as physisorption, chemisorption, or combinations thereof. In one embodiment, up to 10% of the surface area (i.e. outer surface and pore spaces) of the mesoporous silica nanoparticles is covered by the spinel ferrite. Preferably up to 15%, preferably up to 20%, preferably up to 25%, preferably up to 30%, preferably up to 35%, preferably up to 40%, preferably up to 45%, preferably up to 50%, preferably up to 75% of the surface area of the mesoporous silica nanoparticles is covered by the spinel ferrite. In preferred embodiments, at least 25% of the surface area of the mesoporous silica nanoparticles is not covered by the spinel ferrite, and thus the nanoparticles are available for encapsulating other compounds (e.g. platinum complexes). Preferably at least 30%, preferably at least 40%, preferably at least 50%, preferably at least 55%, preferably at least 60%, preferably at least 65%, preferably at least 70%, preferably at least 75%, preferably at least 80%, preferably at least 85% of the surface area of the mesoporous silica nanoparticles is not covered by the spinel ferrite, and thus the nanoparticles are available for encapsulating other compounds (e.g. platinum complexes).

In one or more embodiments, the spinel ferrite is present in an amount of 15-50 wt %, preferably 20-40 wt %, preferably 25-35 wt %, or about 30 wt % relative to a total weight of the nanoformulation. However, in certain embodiments, the spinel ferrite is present in an amount less than 15 wt % or greater than 50 wt % relative to a total weight of the nanoformulation.

In one or more embodiments, the pores of the nanoformulation of the present disclosure have a pore diameter in a range of 10-25 nm, preferably 12-20 nm, more preferably 15-18 nm. In one related embodiment, the nanoformulation has a pore volume in a range of 0.05-0.3 cm³/g, preferably 0.08-0.2 cm³/g, more preferably 0.1-0.18 cm³/g. In another related embodiment, the nanoformulation has a BET surface area in a range of 15-70 m²/g, preferably 20-60 m²/g, more preferably 30-50 m²/g.

The nanoformulation disclosed herein may be paramagnetic, ferromagnetic, or superparamagnetic. In one embodiment, the nanoformulation comprising copper ferrite ($CuFe_2O_4$) may be paramagnetic that is weakly attracted by an externally applied magnetic field and form induced magnetic fields in the direction of the applied magnetic field. In another embodiment, the nanoformulation comprising cobalt ferrite ($CoFe_2O_4$) may be ferromagnetic containing populations of atoms with aligned magnetic moments. In another embodiment, the nanoformulation comprising nickel ferrite ($NiFe_2O_4$) and/or manganese ferrite ($MnFe_2O_4$) may show superparamagnetism which is a form of magnetism appearing in ferromagnetic or ferrimagnetic nanoparticles. In sufficiently small particles, such as the nanoformulation described herein, magnetization can randomly flip direction under the influence of temperature. In the absence of an external magnetic field, the magnetization appears to be zero and the nanoformulation is in the superparamagnetic state. In this state, an external magnetic field is able to magnetize the nanoformulation. Superparamagnetic materials have a magnetic susceptibility larger than that of paramagnets.

Figure 7:
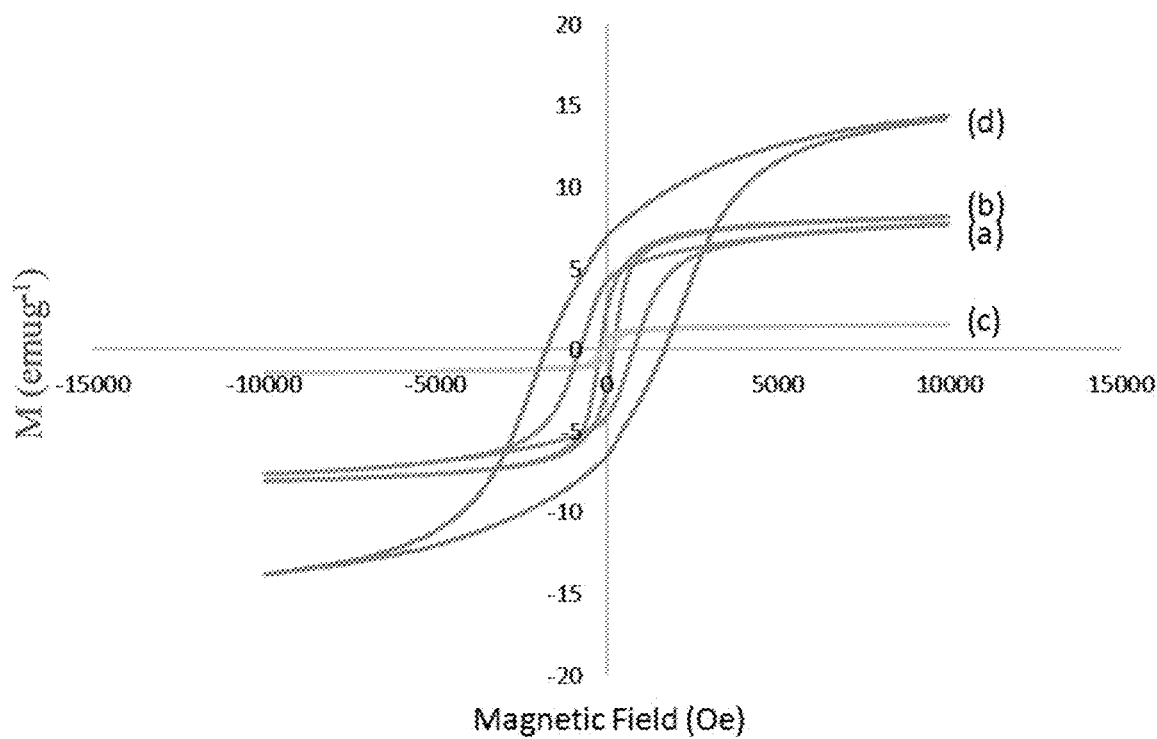
FIG. 7 is an overlay of magnetization curves of nanoformulations containing $CuFe_2O_4$, $NiFe_2O_4$, $MnFe_2O_4$, and $CoFe_2O_4$, respectively obtained by vibrating sample magnetometer (VSM).

The nanoformulation disclosed herein in any of its embodiments may have a saturation magnetization value in a range of 1-20 emu/g, 5-18 emu/g, 7-15 emu/g, or 9-12 emu/g (see FIG. 7). The magnetic susceptibilities may be measured with a laboratory magnetometer such as a vibrating sample magnetometer (VSM), a superconducting quantum interference device, inductive pickup coils, a pulsed field extraction magnetometer, a torque magnetometer, a faraday force magnetometer, and an optical magnetometer.

In one or more embodiments, the nanotherapeutic of the present disclosure comprises a platinum complex encapsulated within pores of the aforementioned nanoformulation. The nanoformulation may be loaded with any platinum complex effective for the treatment of cancer. Preferably, the platinum complex is a platinum(II) complex. In one or more embodiments, the platinum complex is at least one selected from the group consisting of cisplatin, carboplatin, oxaliplatin, nedaplatin, triplatin tetranitrate, phenanthriplatin, picoplatin, and satraplatin. In a preferred embodiment, the platinum complex is at least one of cisplatin, carboplatin, oxaliplatin, and nedaplatin. Most preferably, the platinum complex is cisplatin.

Cisplatin is an anticancer drug that binds to the DNA blocking cell division [S. Dasari, P. B. Tchounwou. Cisplatin in cancer therapy: molecular mechanisms of action. Eur J Pharmacol. 740 (2014) 364-378]. Similar to many other anticancer drugs, cisplatin has off target toxicities that mainly occur in the kidneys, liver, heart, nerves, and ears [L. Galluzzi, L. Senovilla, I. Vitale, J. Michels, I. Martins, O. Kepp, M. Castedo, G. G. Kroemer. Molecular mechanisms of cisplatin resistance. Oncogene 31 (2012) 1869-1883; and S. Dasari, P. B. Tchounwou. Cisplatin in cancer therapy: molecular mechanisms of action. Eur J Pharmacol. 740 (2014) 364-378, each incorporated herein by reference in their entirety]. In addition, most patients develop chemoresistance to cisplatin [L. Galluzzi, L. Senovilla, I. Vitale, J. Michels, I. Martins, O. Kepp, M. Castedo, G. G. Kroemer. Molecular mechanisms of cisplatin resistance. Oncogene 31 (2012) 1869-1883]. Cisplatin-loaded/ $CuFe_2O_4$-coated silica nanoparticles may help overcome these limitations and ensure specific tumor targeting. The encapsulation of cisplatin may prevent off target delivery.

The platinum complex may be encapsulated by the nanoformulation and optionally fill at least some of the pores of the nanoformulation. The platinum complex may be adsorbed onto the surface and/or within the pores of the nanoformulation via physisorption and/or chemisorption interactions such as hydrogen bonds (e.g. Cl . . . H interaction, for platinum complex containing chlorine groups), electrostatic forces, and van der Waals forces.

The platinum complex may be present at a concentration of 0.01-10 mmol/g relative to a total weight of the nanoformulation. Preferably the platinum complex is present at a concentration of 0.05-5 mmol/g, preferably 0.1-2.5 mmol/g, preferably 0.12-2 mmol/g, preferably 0.13-0.18 mmol/g, preferably 0.14-0.17 mmol/g, preferably 0.15-0.16 mmol/g relative to a total weight of the nanoformulation. However, in certain embodiments, the platinum complex is present at a concentration less than 0.01 mmol/g or greater than 10 mmol/g relative to a total weight of the nanoformulation.

The present disclosure further relates to a method of preparing the nanotherapeutic. The method involves the steps of i) mixing an M(II) salt and a Fe(III) salt with the mesoporous silica nanoparticles to form a powdery mixture, ii) calcining the powdery mixture to form a nanoformulation, and iii) mixing the nanoformulation and a platinum complex in an aqueous solution, thereby forming the nanotherapeutic.

Non-limiting examples of the Fe(III) salt include iron(III) nitrate, iron(III) chloride, iron(III) sulfate, iron(III) bromide, iron(III) fluoride, iron(III) phosphate, and mixtures thereof. The iron(III) salt used herein may be in any hydration state, for instance, iron(III) nitrate includes, without limitation, $Fe(NO_3)_3$, $Fe(NO_3)_3.6H_2O$, and $Fe(NO_3)_3.9H_2O$. In certain embodiments, an iron salt having a different oxidation state, such as +2, may be used in addition to or in lieu of the iron(III) salt. In a preferred embodiment, the Fe(III) salt is iron(III) nitrate.

Depending on the chemical identity of "M" of the spinel ferrite intended to be present in the nanotherapeutic, the M(II) salt may be Zn(II), Cu(II), Co(II), Mn(II), Ni(II), Mg(II), Be(II), and/or Ti(II). Preferably, the M(II) salt is at least one selected from the group consisting of Cu(II), Co(II), Mn(II), and Ni(II). Most preferably, the M(II) salt is Cu(II), Ni(II), or both.

Non-limiting examples of the Cu(II) salt include copper(II) nitrate, copper(II) chloride, copper(II) sulfate, copper(II) bromide, copper(II) iodide, and mixtures thereof. The copper(II) salt used herein may be in any hydration state, for instance, copper(II) nitrate includes, without limitation, $Cu(NO_3)_2$, $Cu(NO_3)_2.H_2O$, $Cu(NO_3)_2.2.5H_2O$, $Cu(NO_3)_2.3H_2O$, and $Cu(NO_3)_2.6H_2O$. In certain embodiments, a copper salt having a different oxidation state, such as +1, may be used in addition to or in lieu of the copper(II) salt. In a preferred embodiment, the Cu(II) salt is copper(II) nitrate.

Non-limiting examples of the Ni(II) salt include nickel(II) nitrate, nickel(II) chloride, nickel(II) bromide, nickel(II) iodide, nickel(II) sulfate, nickel(II) acetate, and mixtures thereof. The Ni(II) salt used herein may be in any hydration state, for instance, nickel(II) nitrate includes, without limitation, $Ni(NO_3)_2$, and $Ni(NO_3)_2.6H_2O$. In certain embodiments, a nickel salt having a different oxidation state, such as +3, may be used in addition to or in lieu of the Ni(II) salt. In a preferred embodiment, the Ni(II) salt is nickel(II) nitrate.

Non-limiting examples of the Co(II) salt include cobalt(II) nitrate, cobalt(II) chloride, cobalt(II) bromide, cobalt(II) iodide, cobalt(II) sulfate, cobalt(II) acetate, and mixtures thereof. The Co(II) salt used herein may be in any hydration state, for instance, cobalt(II) nitrate includes, without limitation, $Co(NO_3)_2$, and $Co(NO_3)_2.6H_2O$. In certain embodiments, a cobalt salt having a different oxidation state, such as +3, may be used in addition to or in lieu of the Co(II) salt.

Non-limiting examples of the Mn(II) salt include manganese(II) nitrate, manganese(II) sulfate, manganese(II) chloride, manganese(II) bromide, manganese(II) iodide, manganese(II) acetate, and mixtures thereof. The Mn(II) salt used herein may be in any hydration state, for instance, manganese(II) nitrate includes, without limitation, $Mn(NO_3)_2$, and $Mn(NO_3)_2.4H_2O$. In certain embodiments, a manganese salt having a different oxidation state, such as +3, may be used in addition to or in lieu of the Mn(II) salt.

Preferably, the mesoporous silica nanoparticles may be initially dried to remove volatile impurities. The initial drying may be performed at a temperature of 80-200° C., 100-150° C., or about 120° C. for a period of up to 48 hours, preferably up to 36 hours, or about 24 hours.

In one or more embodiments, mixing the Fe(III) salt and the M(II) salt (e.g. Cu(II), Co(II), Mn(II), and Ni(II)) with the mesoporous silica nanoparticles to form a powdery mixture is conducted in neat (solvent-free) condition. Methods of agitating a powdery mixture include, without limitation, using mortar and pestle, an agitator, a vortexer, a rotary shaker, a magnetic stirrer, a centrifugal mixer, a dual asymmetric centrifugal mixer, or an overhead stirrer. In one embodiment, the powdery mixture is agitated by sonication in an ultrasonic bath or with an ultrasonic probe. In another embodiment, the mixture is mixed with a spatula. Alternatively, mixing the Fe(III) salt and the M(II) salt (e.g. Cu(II), Co(II), Mn(II), and Ni(II)) with the mesoporous silica nanoparticles may be performed in the presence of a solvent such as water and alcohols (e.g. methanol, ethanol, n-propanol, i-propanol, n-butanol) to form a wet mixture. A powdery mixture may be prepared by precipitating and/or drying the wet mixture.

In one or more embodiments, a molar ratio of the M(II) salt (e.g. Cu(II), Co(II), Mn(II), and Ni(II)) to the Fe(III) salt is in a range of 1:0.5 to 1:4, preferably 1:0.7 to 1:3, more preferably 1:0.9 to 1:2, or about 1:1.

The powdery mixture may be calcined in air within a furnace or oven at a temperature of 600-1,100° C., preferably 700-1,000° C., preferably 750-900° C., preferably 800-850° C., though in some embodiments, the powdery mixture may be heated at a temperature lower than 600° C. or higher than 1,100° C. In some embodiments, the powdery mixture may not be heated in air, but oxygen-enriched air, an inert gas, or a vacuum. The powdery mixture may be maintained at the calcining temperature for 1-12 hours, 2-10 hours, 4-8 hours, or about 6 hours. Calcining the powdery mixture produces the nanoformulation.

In another embodiment, it is equally envisaged that the method of producing the nanoformulation may be adapted to other means of dispersing and impregnating the spinel ferrite on the mesoporous silica nanoparticles. Exemplary other means include, but are not limited to, isomorphous substitution, enforced impregnation, vapor-fed flame synthesis, flame spray pyrolysis, sputter deposition, atomic layer deposition, and chemical vapor deposition.

The method further involves mixing the nanoformulation and a platinum complex in an aqueous solution, thereby forming the nanotherapeutic. The platinum complex is the same as previously described.

In one or more embodiments, the aqueous solution is an aqueous solution comprising an alkali salt, an alkaline earth salt, and/or an ammonium salt. Non-limiting examples of salt present in the aqueous solution include sodium or potassium chloride, sodium or potassium bromide, sodium or potassium bicarbonate, sodium or potassium sulfate, sodium or potassium carbonate, and ammonium chloride. Preferably, the aqueous solution is normal saline solution (NSS) that contains sodium chloride at a concentration of 0.8-1.0 wt %, preferably 0.85-0.95 wt %, or about 0.9 wt % relative to a total volume of the solution.

In one embodiment, the platinum complex is present in the aqueous solution at a concentration of 0.1-30 g/L relative to a total volume of the aqueous solution, preferably 0.5-25 g/L, preferably 1-20 g/L, preferably 1.5-15 g/L, preferably 2-10 g/L, preferably 2.5-5 g/L, or about 3 g/L relative to a total volume of the aqueous solution. In a related embodiment, the nanoformulation is present in the aqueous solution at a concentration of 2-600 g/L relative to a total volume of the aqueous solution, preferably 5-500 g/L, preferably 10-400 g/L, preferably 20-300 g/L, preferably 30-200 g/L, preferably 40-100 g/L, preferably 50-75 g/L, or about 60 g/L relative to a total volume of the aqueous solution.

Mixing the nanoformulation and the platinum complex in the aqueous solution may be performed at a temperature of −15-15° C., preferably −10-10° C., preferably −4-4° C. for 2-48 hours, 6-24 hours, or 12-18 hours. Alternatively, the mixing may continue until no net transfer between the platinum complex and the nanoformulation is observed. The net transfer may be determined by monitoring the mixing process using UV-vis, and/or FT-IR spectroscopies. In a preferred embodiment, the mixing is conducted in the absence of light (e.g. keeping the mixture in the dark). The nanotherapeutic containing the platinum complex encapsulated in the pores of the nanoformulation may be collected via filtration, washed with a solution such as water and normal saline solution, and dried in air or in a vacuum.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety).

In one or more embodiments, the nanotherapeutic further comprises one or more pharmaceutically acceptable carriers and/or excipients selected from the group consisting of a buffer, an inorganic salt, a fatty acid, a vegetable oil, a synthetic fatty ester, a surfactant, and a polymer.

In a preferred embodiment, the nanotherapeutic comprises a biocompatible polymer, such as chitosan. Chitosan is a polysaccharide copolymer of N-acetyl-D-glucosamine and D-glucosamine, obtained by the alkaline deacetylation of chitin shells obtained from crustaceans, such as shrimps and crabs. The chitosan may or may not be quaternized chitosan. Derivatives of chitosan, such as chitosan oligosaccharide lactate, trimethylchitosan, and glycol chitosan, which have a higher solubility in water than the unmodified chitosan may be preferred. The chitosan or derivative thereof in the nanotherapeutic may have a weight average molecular weight ranging from 5-100 kDa, preferably 10-80 kDa, more preferably 20-50 kDa. The weight average molecular weight may be measured by gel permeation chromatography. Other exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (maleic anhydride), a polyvinyl alcohols, and copolymers, terpolymers, or combinations or mixtures therein. The copolymer/terpolymer may be a random copolymer/terpolymer, or a block copolymer/terpolymer.

Exemplary buffers include, but are not limited to, phosphate buffers, citrate buffer, acetate buffers, borate buffers, carbonate buffers, bicarbonate buffers, and buffers with other organic acids and salts.

Exemplary inorganic salts include, but are not limited to, calcium carbonate, calcium phosphate, disodium hydrogen phosphate, potassium hydrogen phosphate, sodium chloride, zinc oxide, zinc sulfate, and magnesium trisilicate.

Exemplary fatty acids include, but are not limited to, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, but are not limited to, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethyl-ammonium chloride, and dodecylammonium chloride, and combinations thereof.

The term "active ingredient", as used herein, refers to an ingredient in the nanotherapeutic that is biologically active, for example, the platinum complex. In some embodiments, other active ingredients in addition to the platinum complex may be incorporated into the nanotherapeutic.

In one embodiment, the nanotherapeutic includes a second active ingredient, such as a chemotherapeutic agent or an anticancer agent that is structurally different from the platinum complex, for the treatment or prevention of neoplasm of tumor or cancer cell division, growth, proliferation and/or metastasis in the subject; induction of death or apoptosis of tumor and/or cancer cells; and/or any other forms of proliferative disorder.

The second anticancer agent may be at least one of a mitotic inhibitor; an alkylating agent; an antimetabolite; a cell cycle inhibitor; an enzyme; a topoisomerase inhibitor; a biological response modifier; an anti-hormone; an antiangiogenic agent such as MMP-2, MMP-9 and COX-2 inhibitor; an anti-androgen; a substituted urea such as hydroxyurea; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Exemplary anticancer agents include, but are not limited to, alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; anti-microtubule agents including etoposide, vinblastine, vincristine, teniposide, docetaxel, paclitaxel, vinorelbine, vindesine; cytotoxic antibiotics including daunorubicin, doxorubicin, idarubicin, mitomycin, actinomycin, epirubicin; topoisomerase inhibitors including irinotecan, mitoxantrone, topotecan, and mixtures thereof.

In preferred embodiments, the nanotherapeutic having the active ingredient (e.g. the platinum complex) has pH-dependent controlled release. A pH-dependent controlled release of the active ingredient means that the amount of active ingredient which is released or dissolved in the medium at a certain time interval varies significantly with different pH values. For example, when the nanotherapeutic is exposed in a medium of pH 5 (e.g. acidic tumor microenvironment), at least 35 wt % of the loaded active ingredient is cumulatively released from the nanotherapeutic within 24-80 hours, 36-72 hours, or 48-60 hours, preferably at least 40 wt %, preferably at least 50 wt %, preferably at least 60 wt %, preferably at least 70 wt %, preferably at least 80 wt %, preferably at least 85 wt %, preferably at least 90 wt %, preferably at least 95 wt %, preferably at least 97 wt %, preferably at least 99 wt % of the loaded active ingredient is cumulatively released from the nanotherapeutic within 24-80 hours, 36-72 hours, or 48-60 hours (see FIGS. 8 and 9). While at higher pH levels, for instance at physiological pH 7.4, less than 30 wt % of the loaded active ingredient is cumulatively released from the nanotherapeutic within 24-80 hours, 36-72 hours, or 48-60 hours, preferably less than 25 wt %, preferably less than 20 wt %, preferably less than 15 wt %, preferably less than 10 wt %, preferably less than 5 wt %, preferably less than 2 wt %, preferably less than 1 wt % of the loaded active ingredient is cumulatively released from the nanotherapeutic within 24-72 hours, 36-60 hours, or 42-54 hours.

In one embodiment, the nanotherapeutic having the active ingredient (e.g. the platinum complex) has sustained-release. Sustained-release refers to a release of an active ingredient from a composition or dosage form in which the active ingredient is released over an extended period of time. In one embodiment, sustained-release occurs when there is dissolution of an active ingredient within 0.5-80 hours, preferably within 1-72 hours, more preferably within 24-48 hours after being swallowed. In another embodiment, sustained-release occurs when there is dissolution of an active ingredient within 0.5-80 hours, preferably within 1-72 hours, more preferably within 24-48 hours after entering the intestine. In another embodiment, sustained-release results in substantially complete dissolution after at least 1 hour, preferably after at least 24 hours, more preferably after at least 48 hours following administration. In another embodiment, sustained-release results in substantially complete dissolution after at least 1 hour, preferably after at least 24 hours, more preferably after at least 48 hours following oral administration. In another embodiment, sustained-release results in substantially complete dissolution after at least 1 hour, preferably after at least 24 hours, more preferably after at least 48 hours following rectal administration.

On the contrary, immediate release refers to the release of an active ingredient substantially immediately upon administration. In another embodiment, immediate release occurs when there is dissolution of an active ingredient within 1-20 minutes after administration. Dissolution can be of all or less than all (e.g. about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs. In one embodiment, the nanotherapeutic having the active ingredient (e.g. the platinum complex) has immediate release.

In some embodiments, the active ingredient released from the nanotherapeutic, e.g. the platinum complex, provides utility as an anticancer agent in reducing the viability of cancer cells derived from human cancer cell lines including, but not limited to, breast cancer cell lines (e.g. MCF-7, and SK-BR-3), ovarian cancer cell lines (e.g. NCI-ADR/RES, OVCAR-03), colon cancer cell lines (e.g. HCT-116, HT-29), liver cancer cell lines (e.g. HepG2), lung cancer cell lines (e.g. A549, NCI-H460), brain tumor cell lines (e.g. U251), prostate cancer cell lines (e.g. PC-3), renal cancer cell lines (e.g. 786-0), and melanoma cell lines (e.g. UACC-62).

In some embodiments, the ability of the nanotherapeutic to reduce the viability of cancer cells may be determined by contacting the nanotherapeutic with the cancer cells and then performing cell viability assays. Methods of such assays include, but are not limited to, ATP test, Calcein AM assay, clonogenic assay, ethidium homodimer assay, Evans blue assay, fluorescein diacetate hydrolysis/propidium iodide staining assay, flow cytometry, Formazan-based assays (MTT, XTT), green fluorescent protein assay, lactate dehydrogenase (LDH) assay, methyl violet assay, propidium iodide assay, Resazurin assay, trypan blue assay, and TUNEL assay. In a preferred embodiment, a MTT assay is used.

According to another aspect, the present disclosure relates to a method for treating a proliferative disorder. The method involves administering the nanotherapeutic of the first aspect to a subject in need of therapy.

As used herein, the terms "treat", "treatment", and "treating" in the context of the administration of a therapy to a subject in need thereof refer to the reduction or inhibition of the progression and/or duration of a disease (e.g. cancer), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The term "subject" and "patient" are used interchangeably. As used herein, they refer to any subject for whom or which therapy, including with the compositions according to the present disclosure is desired. In most embodiments, the subject is a mammal, including but not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

In one or more embodiments, the proliferative disorder is cancer. In some embodiments, the disclosed method of the current aspect is for treating cancer of the breast, ovary, cervix, testicle, colon, bladder, lung, blood, brain, rectum, pancreas, skin, prostate gland, stomach, spleen, liver, kidney, head, neck, bone, bone marrow, thyroid gland, or central nervous system. In a preferred embodiment, the cancer is at least one selected from the group consisting of breast cancer, ovarian cancer, cervical cancer, testicular cancer, colon cancer, bladder cancer, and lung cancer. In a more preferred embodiment, the cancer is breast cancer.

As used herein, a subject in need of therapy includes a subject already with the disease, a subject which does not yet experience or exhibit symptoms of the disease, and a subject predisposed to the disease. In preferred embodiments, the subject is a person who is predisposed to cancer, e.g. a person with a family history of cancer. For example, white women or a person with (i) certain inherited genes (e.g. mutated BRCA1, BRCA2, ATM, TP53, CHEK2, PTEN, CDH1, STK11, and PALB2), (ii) radiation occurred to one's chest, and/or (iii) exposure to diethylstilbestrol (DES) are at a higher risk of contracting breast cancer. People who (i) had inflammatory bowel disease, or a genetic syndrome such as familial adenomatous polyposis (FAP) and hereditary non-polyposis colorectal cancer (Lynch syndrome), and/or (ii) consumes a low-fiber and high-fat diet are at a higher risk of contracting colon cancer. People who (i) smoke or regularly breathe in second-hand smoke, (ii) exposed to carcinogens such as asbestos, radioactive substances (e.g., uranium, radon), and/or (iii) inhaled chemicals or minerals (e.g., arsenic, beryllium, cadmium, silica, vinyl chloride, nickel compounds, chromium compounds, coal products, mustard gas, and chloromethyl ethers) are at a higher risk of contracting lung cancer. A person with (i) chronic infection with the hepatitis B virus (HBV) or hepatitis C virus (HCV), (ii) cirrhosis of the liver, (iii) nonalcoholic fatty liver disease, and/or (iv) exposure to aflatoxins is at a higher risk of contracting liver cancer.

Other non-cancerous proliferative disorders that may also be treated by the currently disclosed nanotherapeutic include, without limitation, atherosclerosis, rheumatoid arthritis, psoriasis, idiopathic pulmonary fibrosis, scleroderma, cirrhosis of the liver, lymphoproliferative disorder, other disorders characterized by epidermal cell proliferation such as verruca (warts), and dermatitis, and benign proliferative breast disease such as ductal hyperplasia, lobular hyperplasia, and papillomas.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed with the nanotherapeutics and methods described herein.

Cisplatin is widely prescribed in chemotherapy medications for the treatment of breast, ovarian, cervical, testicular, lung, bladder, head and neck cancers. In one or more embodiments, the platinum complex loaded in the nanotherapeutic is preferably cisplatin and derivatives, e.g. carboplatin, oxaliplatin, nedaplatin, triplatin tetranitrate, phenanthriplatin, picoplatin, satraplatin, lobaplatin, heptaplatin, dicycloplatin, other platinum-based antineoplastic drugs, and mixtures thereof. Preferably, the platinum complex is cisplatin.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", or "pharmaceutically effective amount" refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study.

In one or more embodiments, an effective amount of the nanotherapeutic in a range of 0.5-800 mg/kg, preferably 1-500 mg/kg, more preferably 10-100 mg/kg is administered per body weight of the subject. However, in certain embodiments, the effective amount of the nanotherapeutic is less than 0.5 mg/kg or greater than 800 mg/kg per body weight of the subject.

In treating certain cancers, the best approach is often a combination of surgery, radiotherapy, and/or chemotherapy. Therefore, in at least one embodiment, the nanotherapeutic is employed in conjunction with radiotherapy. In another embodiment, the nanotherapeutic is employed with surgery. The radiotherapy and/or surgery may be before or after the nanotherapeutic is administered.

A treatment method may comprise administering the nanotherapeutic of the current disclosure in any of its embodiments as a single dose or multiple individual divided doses. In some embodiments, the nanotherapeutic is administered at various dosages (e.g. a first dose with an effective amount of 200 mg/kg and a second dose with an effective amount of 50 mg/kg). In some embodiments, the interval of time between the administration of the nanotherapeutic and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the nanotherapeutic is administered once daily for at least 2 days, at least 5 days, at least 6 days, or at least 7 days. In certain embodiments, the nanotherapeutic and one or more additional therapies are administered less than 1 day, less than 1 week, less than 2 weeks, less than 3 weeks, less than 4 weeks, less than 1 month, less than 2 months, less than 3 months, less than 6 months, less than 1 year, less than 2 years, or less than 5 years apart.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, at least 10%, at least 15%, at least 20%, at least 25%, at least 30%, at least 40%, at least 50%, at least 60%, at least 70%, at least 75%, at least 80%, at least 85%, at least 90%, at least 95%, at least 99%, or 100%, relative to the tumor size before treatment. In other embodiments, the size of a tumor after treatment does not reduce but is maintained the same as the tumor size before treatment. Methods of assessing tumor size include, but are not limited to, CT scan, MRI, DCE-MRI and PET scan.

In most embodiments, the method further comprises measuring a concentration of a biomarker and/or detecting a mutation in a biomarker before and/or after the nanotherapeutic of the present disclosure is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC).

Exemplary cancer biomarkers for breast cancer include, without limitation, BRCA1, BRCA2, HER-2, estrogen receptor, progesterone receptor, cancer antigen 15-3, cancer antigen 27.29, carcinoembryonic antigen, Ki67, cyclin D1, cyclin E, and ERβ. Specifically, potentially predictive cancer biomarkers include, without limitation, mutations in genes BRCA1 and BRCA2 for breast cancer. Exemplary biomarkers for colon cancer include, without limitation, carcinoembryonic antigen (CEA), carbohydrate antigen 242 (CA 242), CA 195, CA 19-9, MSI, and 18qLOH. Exemplary biomarkers for lung cancer include, without limitation, CA 125, CA 15-3, EGF receptor, anaplastic lymphoma kinase gene, MET, ROS-1, and KRAS. Exemplary biomarkers for liver cancer include, without limitation, alpha-fetoprotein (AFP), AFP-L3, des-γ-carboxyprothrombin (DCP), GPC3, GP73, cytokeratin 19 (CK 19), osteopontin, IL-6, midkine (MDK), and Annexin A2.

Potentially predictive cancer biomarkers include, without limitation, overexpressions of CEA, NSE, CYFRA-21-1, CA-125, and CA-199 for lung cancer, overexpressions of TYMS, mutations in genes p53 and KRAS for colon cancer, and high concentration levels of AFP, and overexpressions of HSP90α for liver cancer.

The mutation in the biomarker may be detected by procedures such as restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The term "sample" used herein refers to any biological sample obtained from the subject in need of therapy including a single cell, multiple cells, fragments of cells, a tissue sample, and/or body fluid. Specifically, the biological sample may include red blood cells, white blood cells, platelets, hepatocytes, epithelial cells, endothelial cells, a skin biopsy, a mucosa biopsy, an aliquot of urine, saliva, whole blood, serum, plasma, lymph. In some embodiments, the biological sample is taken from a tumor.

The concentration level of the cancer biomarker in a sample may be measured by an assay, for example an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, a concentration of the biomarker is measured before and after the administration. When the concentration of the biomarker is maintained, the method may further comprise increasing the effective amount of the nanotherapeutic by at least 5%, at least 10%, or at least 30%, up to 50%, up to 60%, or up to 80% of an initial effective amount that is in a range of 0.5-800 mg/kg per body weight of the subject. The increased effective amount may be in a range of 0.525-1,440 mg/kg, preferably 5-1,000 mg/kg, more preferably 50-500 mg/kg. The subject may be administered with the increased dosage for a longer period (e.g. 1 week more, 2 weeks more, or 2 months more) than the duration prescribed with the initial effective amount.

In some embodiments, the mutation in the biomarker is detected before administering the composition to identify subjects predisposed to the disease. Alternatively, the biomarkers are measured/detected after each administration.

For example, the measurement may be 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

The examples below are intended to further illustrate protocols for preparing, characterizing the nanotherapeutic, and uses thereof, and are not intended to limit the scope of the claims.

Example 1

Preparation of HYPS Nanoformulations

The support HYPS was purchased from Superior silica, USA.

The support HYPS was predried at 120° C. for 24 h before the preparation of nanoformulations.

For 30% $CoFe_2O_4$; 0.74 g of cobalt nitrate hexahydrate, 1.03 g of iron nitrate nonahydrate was taken and mixed with 1.4 g of HYPS using mortar and pestle and then calcined at 850° C. for 6 h.

For 30% $NiFe_2O_4$; 0.74 g of nickel nitrate hexahydrate, 1.03 g of iron nitrate nonahydrate was taken and mixed with 1.4 g of HYPS using mortar pistol and then calcined at 850° C. for 6 h.

For 30% $CuFe_2O_4$; 0.61 g of copper nitrate trihydrate, 1.01 g of iron nitrate nonahydrate was taken and mixed with 1.4 g of HYPS using mortar pistol and then calcined at 850° C. for 6 h.

For 30% $MnFe_2O_4$; 0.64 g of manganese nitrate tetrahydrate, 1.05 g of iron nitrate nonahydrate was taken and mixed with 1.4 g of HYPS using mortar pistol and then calcined at 850° C. for 6 h.

Example 2

Preparation of the Nanotherapeutics

The cisplatin loading was carried out by dissolving an appropriate amount of cisplatin (30 mg) in normal saline solution (NSS) following our previously published literature [Jermy B R, Acharya S, Ravinayagam V, Alghamdi H S, Akhtar S, Basuwaidan R S (2018) Hierarchical mesosilicalite nanoformulation integrated with cisplatin exhibits target-specific efficient anticancer activity. Appl Nanosci 8, 1205-1220, incorporated herein by reference in its entirety] to yield 30% $CuFe_2O_4$/HYPS-cisplatin. Chitosan wrapped $CuFe_2O_4$/HYPS was prepared as follows. 0.6 wt % chitosan solution was prepared using 10% (v/v) acetic acid solution via overnight stirring. The initial pH of the chitosan solution was 2.77. Then, 1 M NaOH solution was added to the chitosan solution drop wise to increase the pH to 6.4. 1 g cisplatin loaded $CuFe_2O_4$/HYPS was added to the solution and the mixture was kept under stirring for 24 hours. The pH was increased to 7 afterwards. The mixture was kept under stirring for another 24 hours, then centrifuged, washed and dried under vacuum for 48 hours at 37° C.

Example 3

Catalyst Characterization

X-ray diffraction patterns of the SPIONs/silica nanoformulations were analyzed using bench top Rigaku Multiplex system (Rigaku, Japan). Textural characteristics involving surface area and pore size distributions of the parent support and nanoformulations were measured using an ASAP-2020 plus (Micrometrics, USA). Cisplatin functional groups were identified using FT-IR spectroscopy equipped with attenuated total reflectance (ATR) (Perkin Elmer, USA). Surface features of the synthesized materials were characterized by scanning electron microscopy (SEM) and transmission electron microscopy (TEM). For SEM (FEI, Inspect S50, Czech Republic), the prepared powder was dispersed onto double sided tape holder and examined under 20 kV. Depending on the morphology, different magnifications were chosen to capture the representative features of the specimens. For SPIONs/S-16 specimen, the micrographs were taken at representative magnifications of 10,000 and 20,000×, while 20,000 and 50,000× were applied for SPIONs/HYPS and SPIONs/MSU-F specimens. TEM samples were prepared by dispersing a small amount of sample in ethanol and deposited onto TEM grids. The grids were examined by a TEM instrument (FEI, Inspect S50, Czech Republic) at a working voltage of 80 kV. Several images were acquired to measure the particle size and calculate an average size. The particle size was measured using Gatan digital micrograph software. The results are displayed in the form of size histogram for each prepared sample.

Example 4

Drug Adsorption Study

In cisplatin adsorption study, spinel ferrite/silica nanoformulations (600 mg) were independently mixed with 30 mg of cisplatin in 10 mL of saline solution under ice cooled dark environment. After stirring overnight, the solution mixture was filtered, and washed with 15 mL normal saline solution. Then the amount of adsorbed cisplatin was calculated via UV-visible spectroscopy using the wavelength at 208 nm.

Example 5

Drug Release Study

The cumulative cisplatin release was studied using different nanoformulations involving HYPS (i.e. nanotherapeutics). Cellulose membrane dialysis tubing was activated, and drug delivery analysis was performed by immersing the bag containing 30 mg of nanoformulations in 50 mL of phosphate buffered saline (PBS) at pH 5.6. The release condition was performed under stabilized temperature of 37° C. At a specified time interval, a 10 mL solution was removed and analyzed using UV-visible spectroscopy.

Example 6

In-Vitro Study on MCF-7 Cells

In this disclosure, the antitumor effect of nanotherapeutics including cisplatin loaded 30 wt % $CuFe_2O_4$/HYPS and 30 wt % $CuFe_2O_4$/HYPS/chitosan was tested on human mammary adenocarcinoma cell line, MCF-7. Cells were maintained in DMEM (Dulbecco's Modified Eagle Medium) (Gibco, life technologies) supplemented with 10% heat inactivated fetal bovine serum (HI-FBS) (Gibco, life technology), 1% Penicillin Streptomycin (100×—Gibco, life technology), and 1% MEM NEAA (MEM non-essential amino acids) (100×—Gibco, life technology). Cells were kept in a humidified incubator at 37° C. with 5% $CO_2$. For the experimental setup, MCF-7 cells were seeded on a 96-well plate at a density of 20,000 cells/well. On the next day, cells were shifted to the starve media (0.5% HI-FBS containing media) for 24 h before treatment.

Treatment Conditions:
  Group A—$CuFe_2O_4$
  Group B—Nanomaterial (i.e. mesoporous silica)
  Group C—Nanomaterial+$CuFe_2O_4$ (i.e. nanoformulation)
  Group D—Cisplatin
  Group E—Cisplatin+Nanomaterial+$CuFe_2O_4$ (i.e. nanotherapeutic)
  Group F—Cisplatin+Nanomaterial+$CuFe_2O_4$+Chitosan Cells were treated for 48 hours with the following conditions: group A ($CuFe_2O_4$), group B (nanomaterial), group C (nanomaterial+$CuFe_2O_4$), group D (cisplatin), group E (cisplatin+nanomaterial+$CuFe_2O_4$), and group F (cisplatin+nanomaterial+$CuFe_2O_4$+chitosan). For groups B, C, E, and F, treatment concentrations were as follows: 0.025, 0.05, 0.1, and 0.5 mg/mL. To accurately reflect the concentration of $CuFe_2O_4$ (group A), and cisplatin (group D) that is encapsulated within these nanoparticles, the drug loading experiments were used to calculate the actual concentration of each in the other groups. Therefore, treatment concentrations for group A were as follows: 0.0084, 0.0168, 0.0336, and 0.168 mg/mL. Treatment concentrations used in this experiment for group D were as follows: 0.001125, 0.00225, 0.0045, 0.0225 mg/mL.

Example 7

Cell Viability—MTT Assay

The viability of cells was tested using 3-(4,5-dimethylthiazol-2-yl)-2,5-diphenyltetrazolium bromide (MTT) assay. It is based on the ability to reduce MTT relative to formazan crystals. The assay was performed using previously published protocols [Mosmann T. Rapid colorimetric assay for cellular growth and survival: application to proliferation and cytotoxicity assays. J. Immunol Methods. 1983 Dec. 16; 65(1-2): 55-63]. Briefly, MTT (Sigma-Aldrich) was dissolved in PBS at a concentration of 5 mg/mL. Working solution of MTT was prepared at a final concentration of 0.5 mg/mL (10 μL of stock MTT+90 μL 1×PBS/well). The 96 wells plate was washed twice with 1×PBS and 100 μL of MTT working solution was dispended in all wells. An MTT background control was included, in which MTT working solution was added to empty wells (no cells). The plate was incubated for three hours at 37° C., followed by the addition of 100 μL of acidified isopropanol solubilizing solution (0.04 N HCl isopropanol). The change in color intensity was measured at 570 nm wavelength using SYNERGY-neo2 BioTek ELISA reader. Each condition was performed in triplicates. The reading of each triplicate was averaged and subtracted from the averaged MTT background control reading. Each condition was compared to the control (no treatment) wells. The following equation was used to calculate the % of cell viability:

$$\% \text{ Cell Viability} = \frac{\text{averaged sample read}}{\text{averaged control read}} \times 100$$

Example 8

Statistical Analysis

Cell viability assay data represent four independent experiments. Statistical analysis was performed using Prism 7 software (GraphPad, La Jolla, Calif.). Analysis was performed using two-way ANOVA with Dunnett's post hoc test. *$p<0.05$; $p<0.01$; *$p<0.001$; ****$p<0.0001$ versus control.

Example 9

Results and Discussions: Nanoformulations

FIG. 1 shows the XRD diffraction patterns of 30% $CuFe_2O_4$ loaded on HYPS using dry impregnation technique. The presence of a characteristics broad peak due to amorphous siliceous framework was observed between 15-30°. In case of metal oxides, the diffraction patterns correlate with the cubic phase of copper ferrite (JCPDS 77-0010). However, the presence of relatively less crystalline $CuFe_2O_4$ nanoparticles demonstrated by weak peaks and increased broadness clearly indicates the presence of small nanosized nanoparticles. Such trend indicates the lack of crystallization at spherical nanopores of HYPS (FIG. 1).

Figure 2:
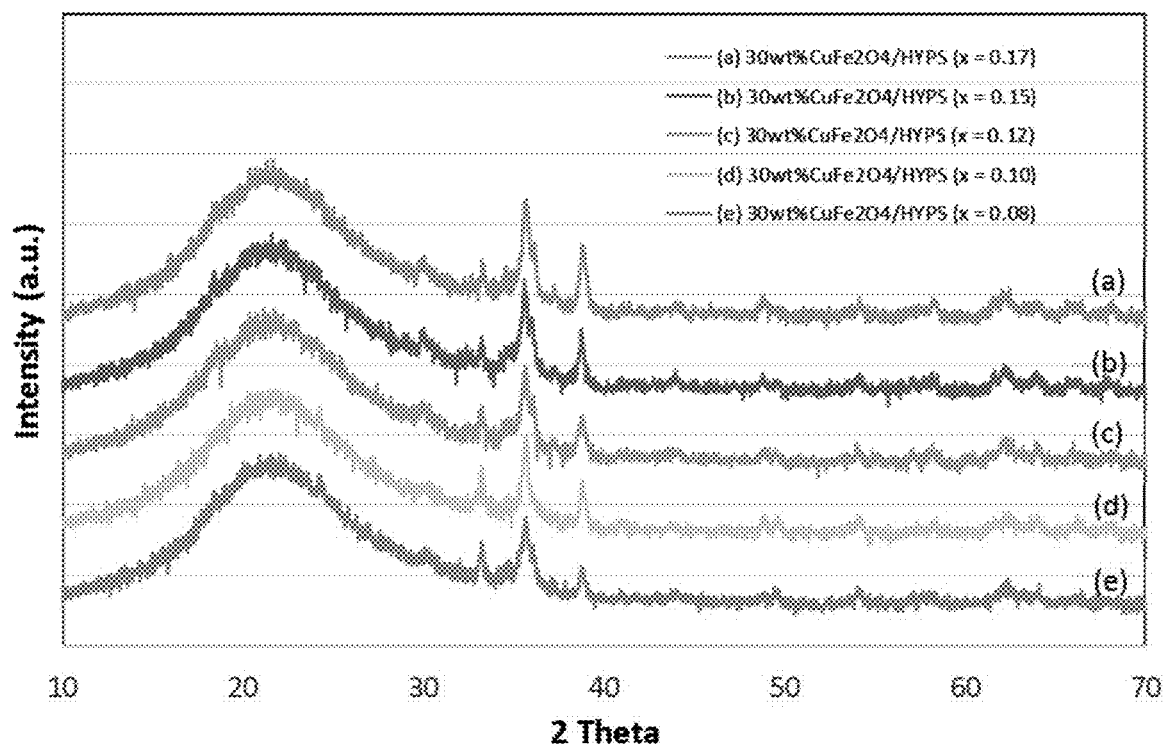
FIG. 2 is an overlay of XRD patterns of nanoformulations containing copper ferrite with various copper contents.

As shown in FIG. 2, the intensity of spinel increases with increasing copper content. This shows that the occupation of copper in octahedral positions may improve the crystallinity.

Figure 3:
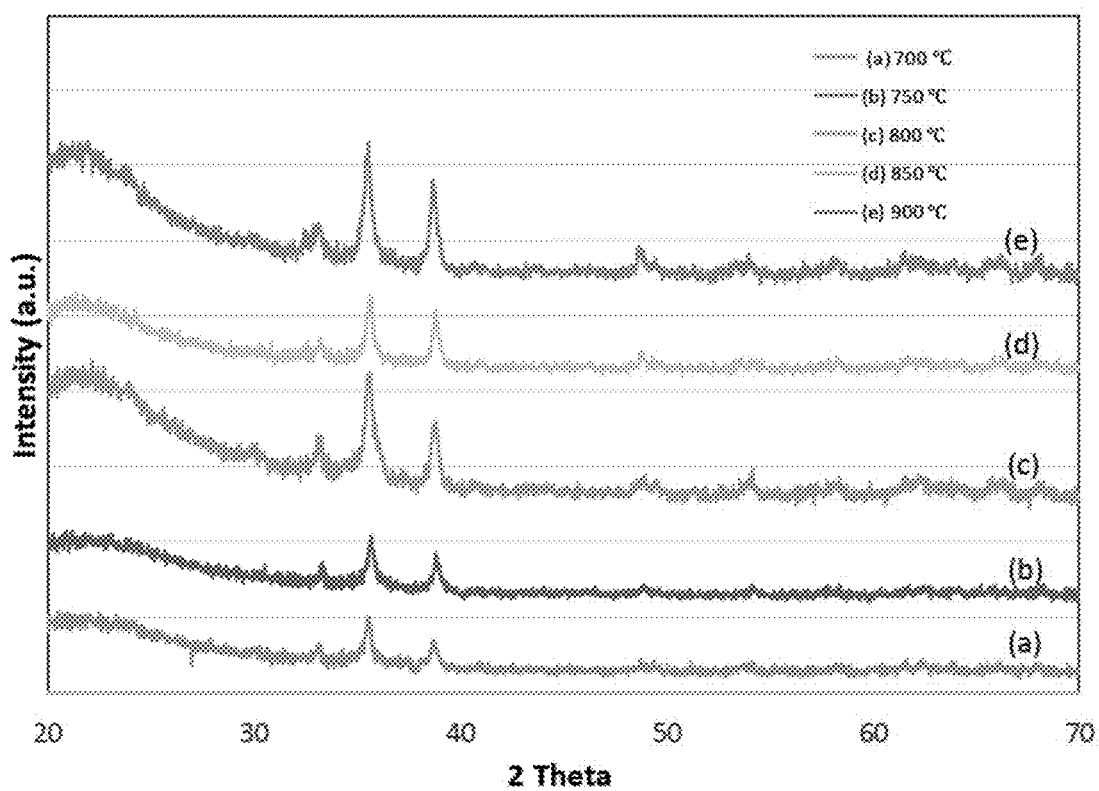
FIG. 3 is an overlay of XRD patterns of nanoformulations containing copper ferrite calcined at a temperature of 700° C., 750° C., 800° C., 850° C., and 900° C., respectively.

XRD diffraction patterns of $CuFe_2O_4$/HYPS calcined at different temperatures ranging between 700-900° C. are shown in FIG. 3. The intensity of $CuFe_2O_4$ main intensity peak at 35° tends to increase with increasing calcination temperature. However, at lower calcination temperatures pure spinel components dominate, while increasing temperature tends to produce mixed phase along with copper iron oxide though in a minor amount. The pattern shows spinel crystal growth with increasing temperature, while presence of broad peak corresponding to silica even at high temperature of 900° C. shows the preservation of amorphous characteristics. Najmoddin et al. [N. Najmoddin, A. Beitollahi, M. Muhammed, N. Ansari, E. Devlin, S. Majid Mohseni, H. Rezaie, D. Niarchos, J. Åkerman, M. S. Toprak, Effect of nanoconfinement on the formation, structural transition and magnetic behavior of mesoporous copper ferrite, Journal of Alloys and Compounds 598 (2014) 191-197, incorporated herein by reference in its entirety] has reported that cubic phase of $CuFe_2O_4$ can be effectively stabilized inside the pore channels of silica due to the suppression of John-Teller distortion. In addition, based on the characteristic support studies (XRD and TEM), a significant contribution of silica cages was confirmed in maintaining the super magnetic property at room temperature.

Figure 4A:
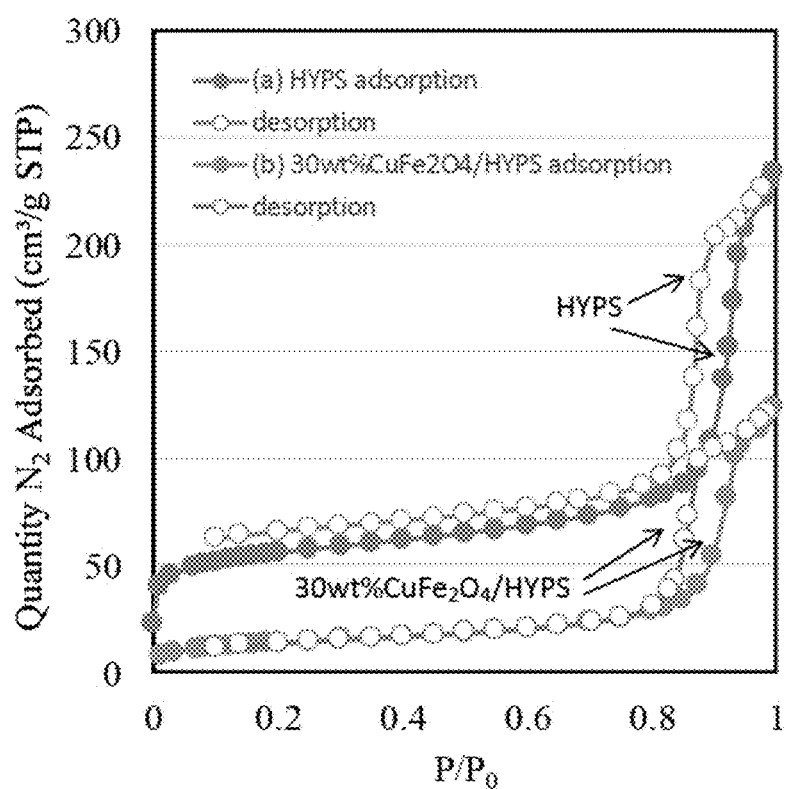
FIG. 4A is an overlay of $N_2$ sorption isotherms of mesoporous silica nanoparticles (HYPS) and nanoformulation containing copper ferrite (30 wt % $CuFe_2O_4$/HYPS), respectively.
Figure 4B:
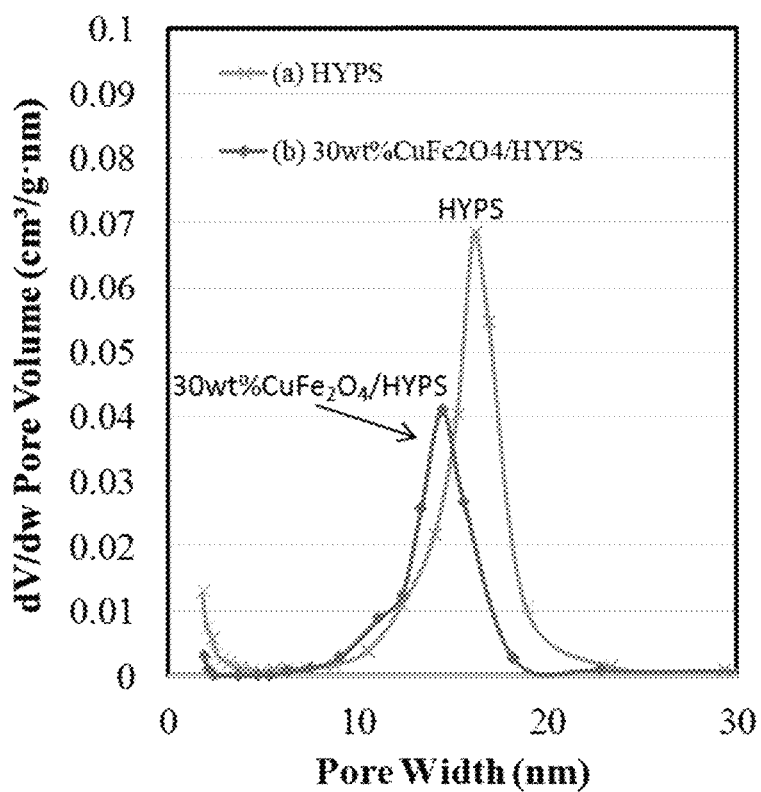
FIG. 4B is a graph showing pore size distributions of mesoporous silica nanoparticles (HYPS) and nanoformulation containing copper ferrite (30 wt % $CuFe_2O_4$/HYPS), respectively.

The surface area and pore size distributions of HYPS and $CuFe_2O_4$/HYPS were analyzed using nitrogen adsorption technique. FIGS. 4A and 4B show the isotherms (adsorption and desorption) and pore size distributions for (a) HYPS and (b) 30% $CuFe_2O_4$/HYPS, respectively. Monodispersed spherical silica HYPS shows a type IV isotherm corresponding to the presence of mesopores. The silica hysteresis loop tends to be present at higher relative pressures of $p/p_0 > 0.8$. HYPS exhibits a surface area of 170 $m^2/g$, pore volume of 0.35 $cm^3/g$ with intermediate average pore size distributions of 8.3 nm. After spinel loading, about 28% reduction in BET surface area was observed, while a significant increase in the pore size from 8.3 nm to 16.0 nm was seen. The trend clearly shows the accumulation of spinel ferrite nanoparticles at the external pores of HYPS.

TABLE 1

Textural characteristics of HYPS and 30 wt % spinel ferrites/HYPS.

| Sample | Spinel Ferrite Loading (wt %) | BET Surface area ($m^2/g$) | BJH adsorption cumulative surface area ($m^2/g$) | Pore volume ($cm^3/g$) | PD (nm) |
|---|---|---|---|---|---|
| HYPS | — | 170 | 85 | 0.35 | 8.3 |
| $CuFe_2O_4$/HYPS | 30 | 47 | 45 | 0.18 | 16.0 |
| $NiFe_2O_4$/HYPS | 30 | 29 | 30 | 0.12 | 17.1 |
| $MnFe_2O_4$/HYPS | 30 | 21 | 21 | 0.10 | 18.4 |

Figure 5A:
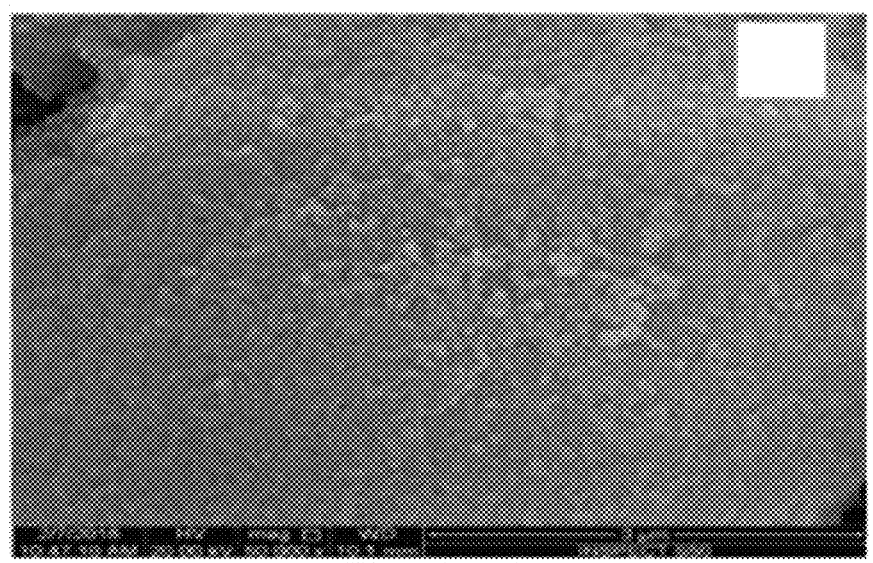
FIG. 5A is a scanning electron microscope (SEM) image of mesoporous silica nanoparticles.
Figure 5B:
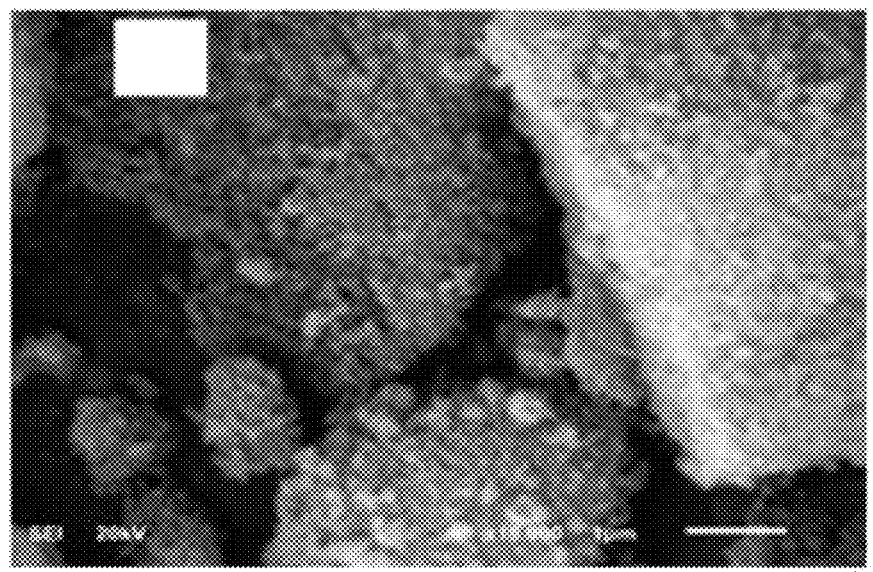
FIG. 5B is a SEM image of nanoformulation containing copper ferrite.
Figure 5C:
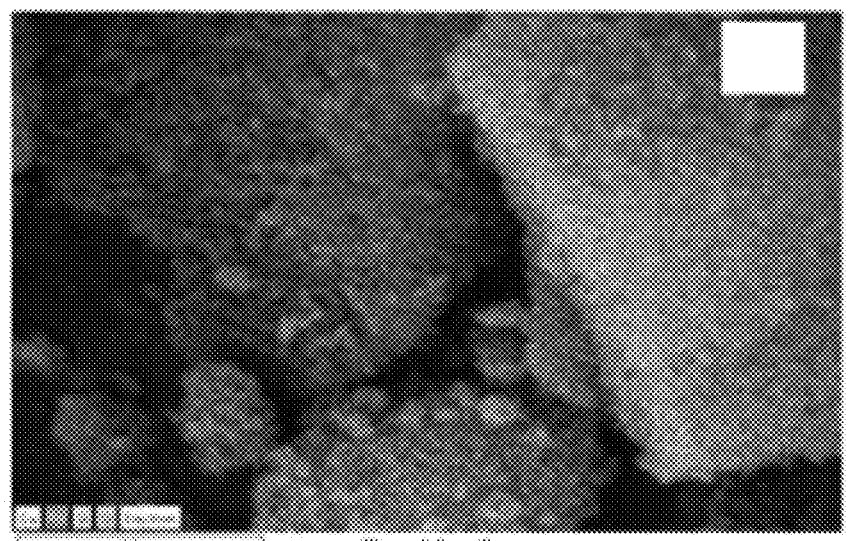
FIG. 5C is an energy-dispersive spectroscopy (EDS) layered image of nanoformulation containing copper ferrite.
Figure 5D:
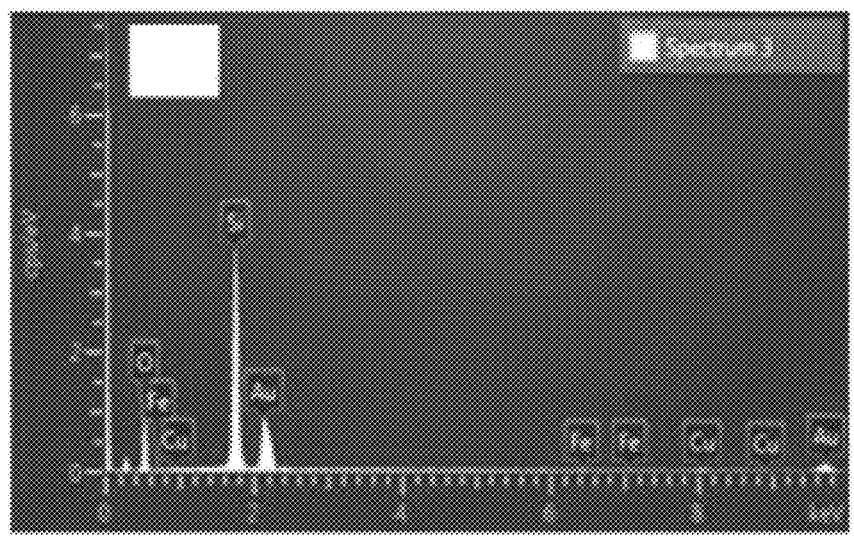
FIG. 5D is an EDS spectrum of nanoformulation containing copper ferrite.
Figure 5E:
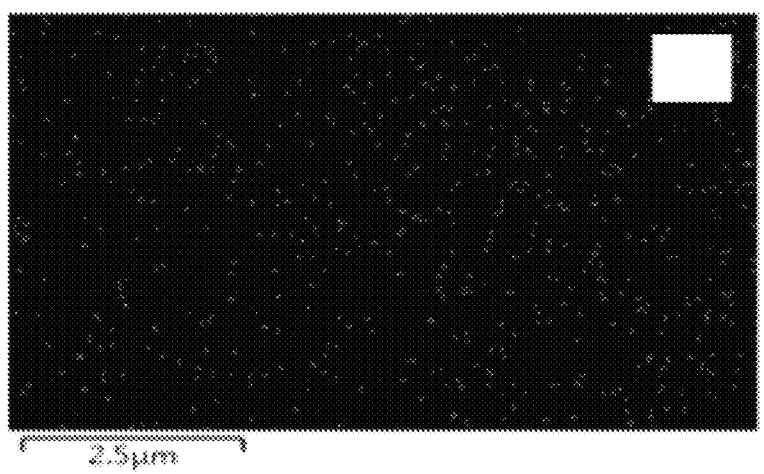
FIG. 5E is an elemental mapping of iron of nanoformulation containing copper ferrite.
Figure 5F:
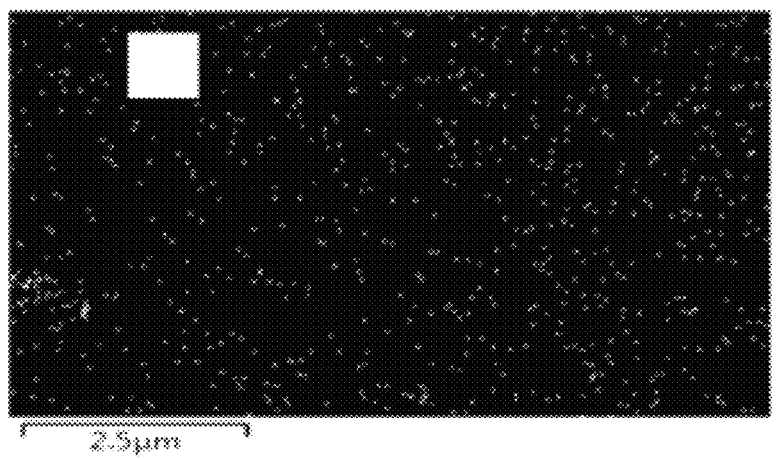
FIG. 5F is an elemental mapping of copper of nanoformulation containing copper ferrite.

The surface morphology of parent HYPS and 30% $CuFe_2O_4$/HYPS was analyzed through SEM at two different scale bars of 3 and 1.0 µm (FIGS. 5A and 5B). Parent HYPS showed the presence of monodispersed spherical silicas distributed uniformly in the range of about 80 nm (FIG. 5A). After spinel loading, a different surface morphology was observed. The parent nanometer sized spherical spheres were found to be impregnated by nano spinels that were interrelated with each other (FIG. 5B). The $CuFe_2O_4$ nanoparticles were microscopically captured using EDX-mapping analysis to observe the location of Cu and iron oxide over HYPS support. The mapping of HYPS showed homogeneous silica particles consistence with the SEM analysis. In case of copper ferrite nanoparticles, a uniform distribution of Cu and Fe indicates mixed metal oxide formations homogeneously spread over silica support (FIGS. 5E and 5F). In addition, additional small nanoclusters of Cu species were also observed.

Figure 6:
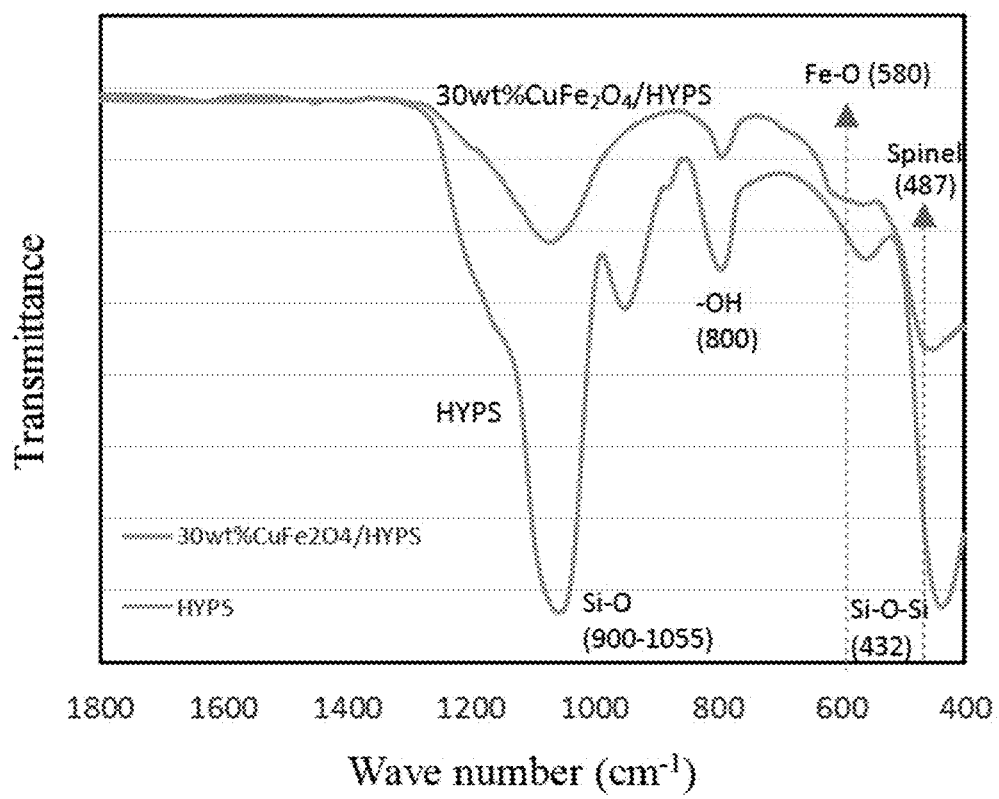
FIG. 6 is an overlay of FT-IR spectra of mesoporous silica nanoparticles (HYPS) and nanoformulation containing copper ferrite (30 wt % $CuFe_2O_4$/HYPS), respectively.

The FT-IR spectra of silica HYPS showed several peaks corresponding to Si—O—Si stretching and vibration, hydroxyl, and Si—O bond at around 432 $cm^{-1}$, 800 $cm^{-1}$, and between 900-1055 $cm^{-1}$, respectively. Notably, the peak intensity of silica at around 432 $cm^{-1}$ and 900-1055 $cm^{-1}$ corresponding to silanol groups decreased after $CuFe_2O_4$ deposition (FIG. 6). Such pattern indicates the external surface occupation of spinel over HYPS. The peak position of 30% $CuFe_2O_4$/HYPS shows rearrangements of peak position at about 487 $cm^{-1}$ with tetrahedral and octahedral sites of $MFe_2O_4$. The absorption band at 580 $cm^{-1}$ clearly shows the presence of Fe—O bond of spinel present over HYPS support.

The magnetic properties of spinel ferrite/HYPS nanocomposites (i.e. nanoformulations) were measured using vibrating sample magnetometer (VSM). FIG. 7 shows an overlay of VSM of a) 30% $CuFe_2O_4$/HYPS, (b) 30% $NiFe_2O_4$/HYPS, (c) 30% $MnFe_2O_4$/HYPS, and (d) 30% $CoFe_2O_4$/HYPS, respectively. Based on the composition of spinel ferrites, different magnitudes of magnetization were observed. The magnetization generated by various spinel ferrites over HYPS was in the following order: 30 wt % $CoFe_2O_4$/HYPS (14.15 emug$^{-1}$)>30 wt % $NiFe_2O_4$/HYPS (7.73 emug$^{-1}$)>30 wt % $CuFe_2O_4$/HYPS (7.65 emug$^{-1}$)>30 wt % $MnFe_2O_4$/HYPS (1.49 emug$^{-1}$). Reducing the particle size tends to decrease the magnetization saturation due to noncollinear spin arrangements at or near the surface of particles [B. Martinez, X. Obradors, L I. Balcells, A. Rouanet, C. Monty, Low temperature surface spin-glass transition in γ-$Fe_2O_3$ nanoparticles, Phys. Rev. Lett. 80 (1) (1998) 181-183, incorporated herein by reference in its entirety], which in turn influences the response of material to the external magnetic field. The spinel properties are influenced by the cation distribution over the A and B sites, as presence of different cations tends to influence the magnetic and electrical property. Copper ferrites are known ferrites, where Zn atoms are substituted at the tetrahedral site of Cu, for variable magnetization property. In the present case, 30 wt % $CuFe_2O_4$/HYPS showed paramagnetic behavior, while cobalt ferrite/silica showed ferromagnetism, which are reported to occur due to anti parallel spins of $Fe^{3+}$ located at tetrahedral sites, while $M^{2+}$ at octahedral sites. It has been shown that presence of small sized nanoclusters at the walls of hexagonal shaped MCM-41 tends to form super paramagnetic interactions among $Fe^{3+}$ species, while large nanoclusters contribute towards ferromagnetic property [S. Dasari, P. B. Tchounwou. Cisplatin in cancer therapy: molecular mechanisms of action. Eur J Pharmacol. 740 (2014) 364-378, incorporated herein by reference in its entirety]. In the present study, nickel ferrite/HYPS showed most pronounced super paramagnetic behavior with narrow hysteresis followed by copper ferrite/HYPS. Such trend demonstrates the formation of small nanosized nickel and copper spinel clusters over HYPS (FIG. 7, lines "a" and "b"). $MnFe_2O_4$/HYPS showed the super paramagnetic behavior but with much lower magnetization (FIG. 7, line "c"). $CoFe_2O_4$/HYPS generated the highest magnetization with a broad hysteresis loop indicating a shift towards ferromagnetic behaviour compared to other three nanocomposites. Such magnetic trend shows the formation of large nanoclusters (FIG. 7, line "d").

Example 10

Results and Discussions: Nanotherapeutic

Figure 8:
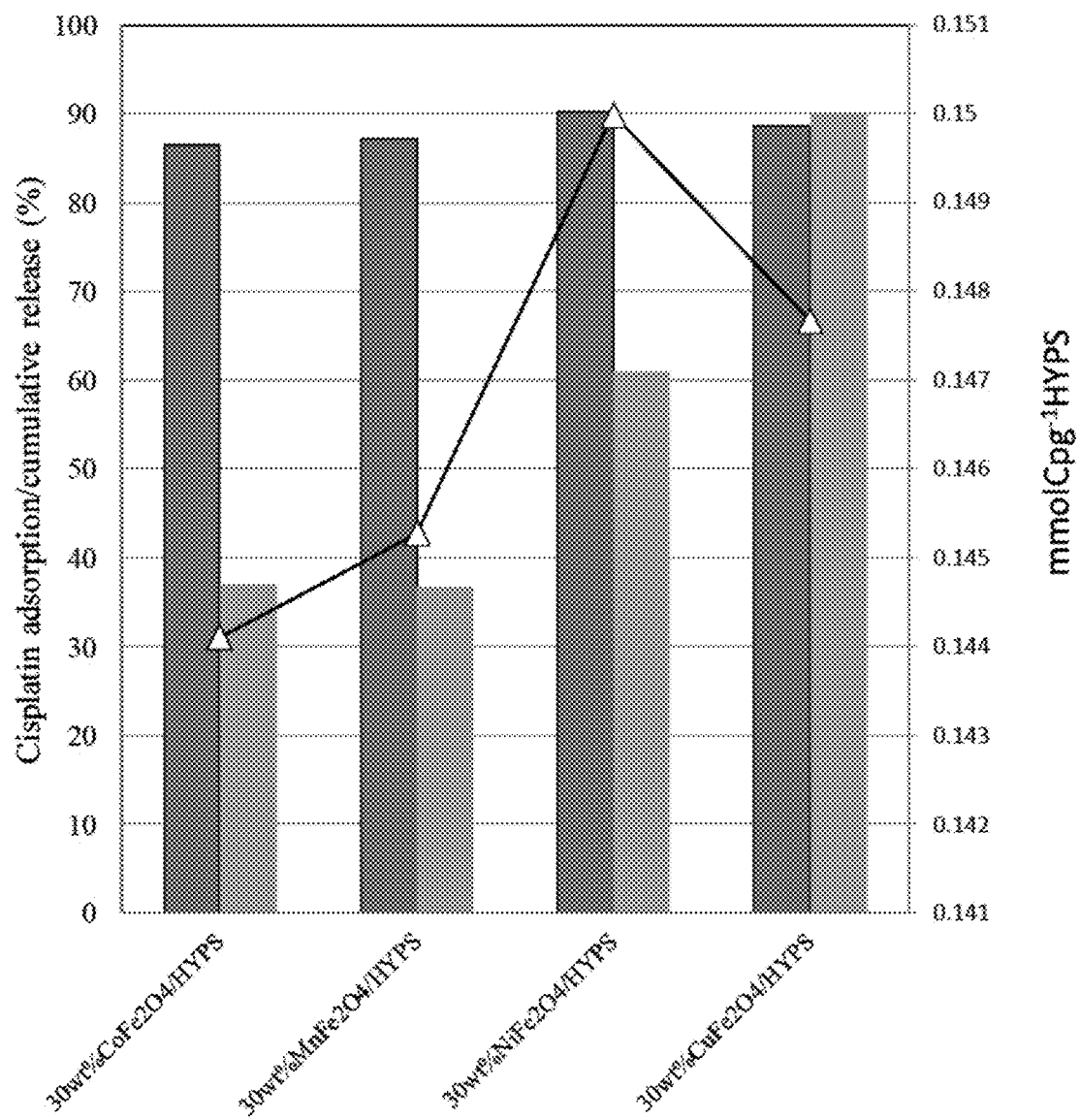
FIG. 8 is a bar graph showing the cisplatin adsorption/cumulative release (%) over 24 hours at pH 5 as well as cisplatin loading capacity (mmol cisplatin/1 g of HPYS) of nanotherapeutics containing $CuFe_2O_4$, $NiFe_2O_4$, $MnFe_2O_4$, and $CoFe_2O_4$, respectively.

FIG. 8 summarizes the cisplatin adsorption capacity and percentage cumulative release in tumor at pH 5 for 24 h over 30% $CuFe_2O_4$/HYPS, 30% $NiFe_2O_4$/HYPS, 30% $MnFe_2O_4$/HYPS and 30% $CoFe_2O_4$/HYPS, respectively. In case of cisplatin adsorption, 4 nanoformulations showed an adsorption between 86-90%. In particular, $CoFe_2O_4$/HYPS and $CuFe_2O_4$/HYPS showed adsorption of about 86.5% and 88.6%, respectively. On the other hand, $MnFe_2O_4$/HYPS and $NiFe_2O_4$/HYPS showed a greater adsorption of 87.2% and 90.3%, respectively. The cisplatin release profile calculated based on mmol of cisplatin per gram of nano support showed a significant variation with respect to cisplatin release. For instance, though cisplatin adsorption remains similar among nanoformulations, $NiFe_2O_4$/HYPS and $CuFe_2O_4$/HYPS showed the highest cisplatin release, which was followed by $MnFe_2O_4$/HYPS and $CoFe_2O_4$/HYPS.

Figure 9:
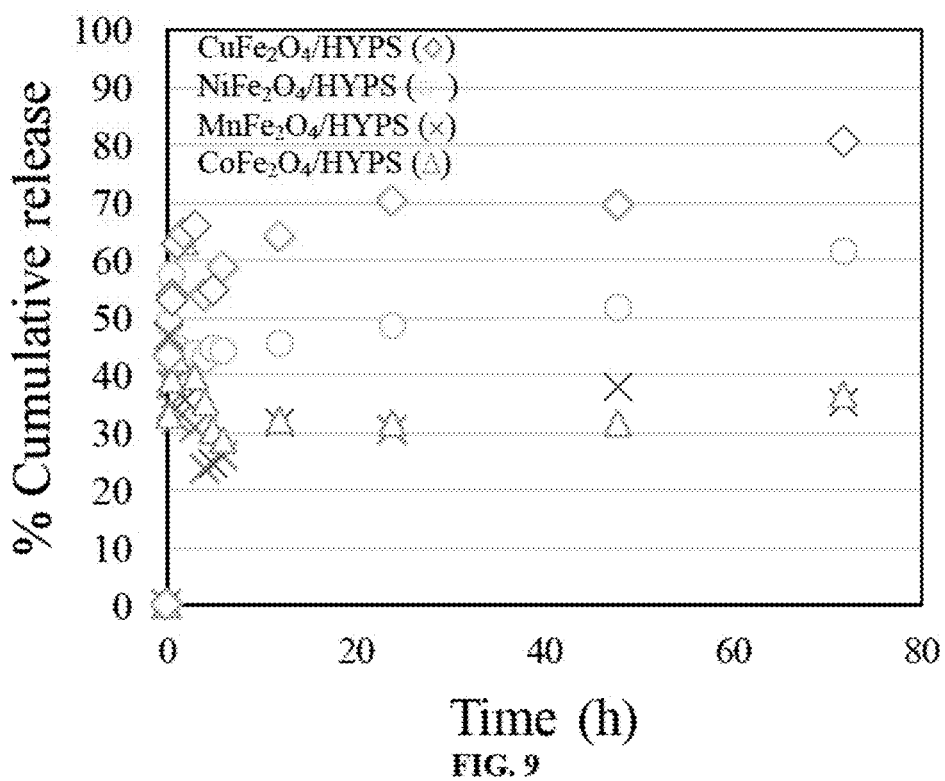
FIG. 9 shows cisplatin release profiles of nanotherapeutics containing $CuFe_2O_4$, $NiFe_2O_4$, $MnFe_2O_4$, and $CoFe_2O_4$, respectively, over 72 hours under simulated tumor acidic conditions (i.e. pH 5, 37° C.).

The drug release profile of spinel ferrite-based system $MFe_2O_4$=Ni, Co, Cu and Mn) was studied at simulated tumor acidic pH conditions (pH 5) at 37° C. for 72 h (FIG. 9). The spinel ferrites studied include 4 types of metal composites Ni, Co, Cu and Mn. The ratio of cisplatin (mmol) per gram of spinel HYPS nanosupport was maintained at 0.15. Among the different nanoformulations, the order of cisplatin drug release rate was in the following order: 30 wt % $CuFe_2O_4$/HYPS>30 wt % $NiFe_2O_4$/HYPS>30 wt % $MnFe_2O_4$/HYPS 30 wt % $CoFe_2O_4$/HYPS, respectively. 30 wt % $CuFe_2O_4$/HYPS showed the highest percentage cumulative cisplatin release of 90% within 72 h. The study shows that fabrication of HYPS with 30 wt % $CuFe_2O_4$ is not affecting cisplatin release at acidic tumor condition. 30 wt % $NiFe_2O_4$/HYPS showed the second-best formulation over HYPS. The percentage release was lower at about 61%, which indicates the positive effect of $CuFe_2O_4$/HYPS with respect to cisplatin release rate. This trend signifies the importance of synergism among $CuFe_2O_4$, cisplatin, and HYPS support, which facilitates releasing cisplatin efficiently (FIG. 9). However, cisplatin over Mn and Co based spinel ferrite showed an initial burst release of 75% within about 30 min, which then reduced to 53% at 72 h. This clearly indicates that in addition to $CuFe_2O_4$/HYPS, $NiFe_2O_4$/HYPS formulation can be another potential nanocarrier for drug delivery application.

Figure 10:
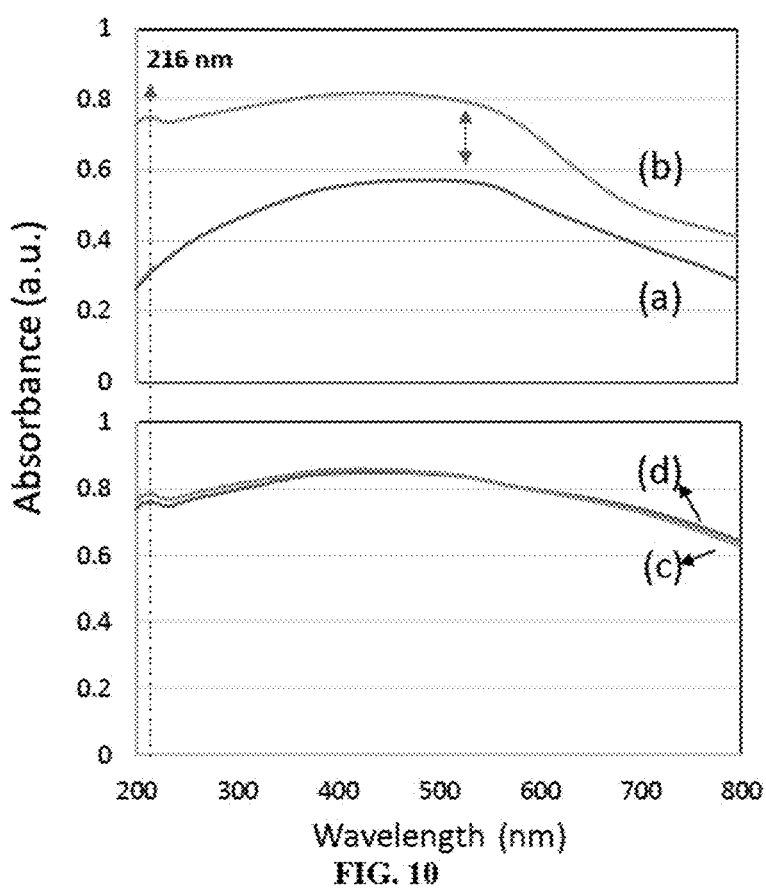
FIG. 10 is an overlay of UV-vis diffuse reflectance spectroscopy (DRS) spectra of nanoformulations containing $CuFe_2O_4$ (a), nanotherapeutic containing $CuFe_2O_4$ (b), nanoformulations containing $MnFe_2O_4$ (c), and nanotherapeutic containing $MnFe_2O_4$ (d), respectively.
Figure 11:
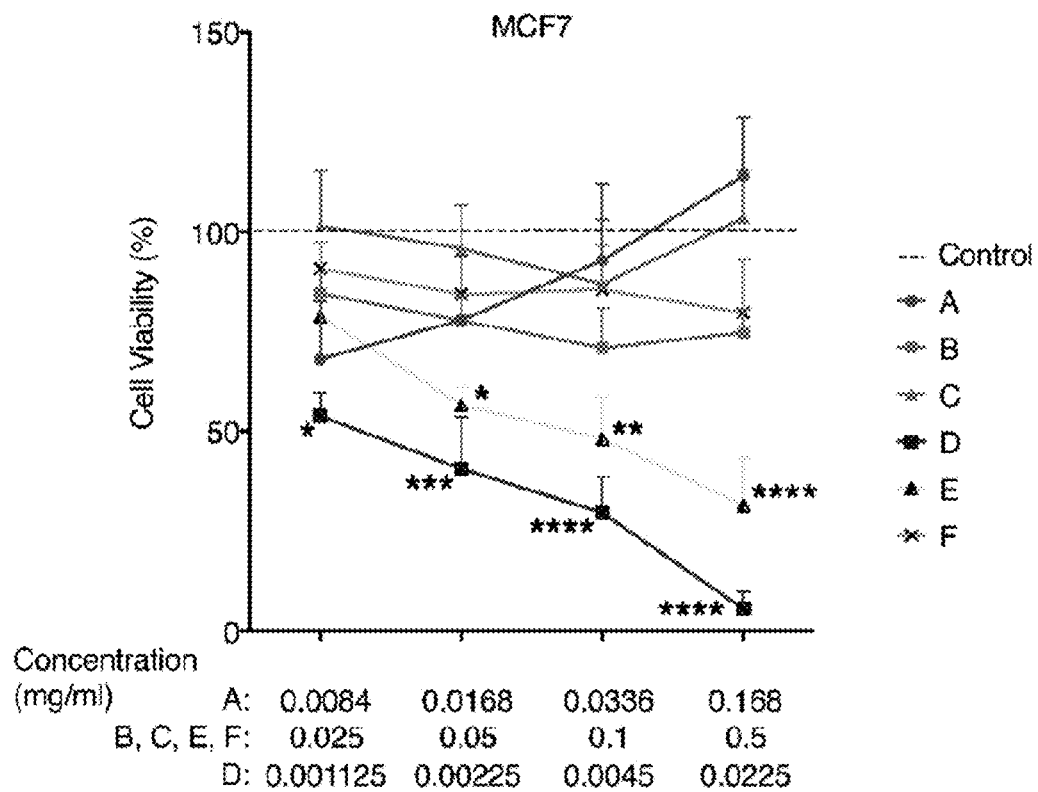
FIG. 11 shows MCF-7 cell viability MTT assay results of $CuFe_2O_4$ (group A), mesoporous silica nanoparticles (group B), nanoformulation containing $CuFe_2O_4$ (group C), cisplatin (group D), nanotherapeutic containing $CuFe_2O_4$ (group E), and nanotherapeutic containing $CuFe_2O_4$ and chitosan (group F), respectively.

In order to understand the high cisplatin release ability of 30 wt % $CuFe_2O_4$/HYPS, the coordination environment of cisplatin over 30 wt % $CuFe_2O_4$/HYPS (active sample) and 30 wt % $MnFe_2O_4$/HYPS (in active sample) were analyzed using diffuse reflectance spectroscopy. Ferrites are cubic spinels containing tetrahedral and octahedral crystalline sites [N. Najmoddin, A. Beitollahi, E. Devlin, H. Kavas, S. M. Mohseni, J. Akerman, D. Niarchos, H. Rezaie, M. Muhammed, M. S. Toprak, Magnetic properties of crystalline mesoporous Zn-substituted copper ferrite synthesized under nanoconfinement in silica matrix, Microporous and Mesoporous Materials 190 (2014) 346-355]. Both support samples before cisplatin adsorption showed wide and strong absorption between 200-700 nm, characteristics of spinel structure (FIG. 10 lines "a" and "c"). Remarkably, after platinum adsorption $CuFe_2O_4$/HYPS sample showed enhanced peak absorption up to 700 nm, while no significant improvement in the coordination site was observed over $MnFe_2O_4$/HYPS (FIG. 10, lines "b" and "d"). In particular, a small absorption at around 224 nm showed the presence of tetrahedral coordinated Pt nanoclusters, while a significant enhancement of absorption peak at 350-600 nm shows the presence of octahedral coordinated Pt species (FIG. 10, line "b"). The presence of such strong bonds of tetrahedral and octahedral Pt species indicates high dispersity and interaction of Pt on HYPS silica support. Previously, it was shown that such Pt species over mesosilicalite exerted high cytotoxic effect against HeLa ($LC_{50}$=0.02 mg/ml), MCF-7 ($LC_{50}$=0.05 mg/ml), while less toxic towards normal fibroblast cells ($LC_{50}$=0.5 mg/ml) [Jermy B R, Acharya S, Ravinayagam V, Alghamdi H S, Akhtar S, Basuwaidan R S (2018) Hierarchical mesosilicalite nanoformulation integrated with cisplatin exhibits target-specific efficient anticancer activity. Appl Nanosci 8, 1205-1220, incorporated herein by reference in its entirety]. Therefore, the activity of nanotherapeutic (cisplatin loaded 30 wt % $CuFe_2O_4$/HYPS) against MCF-7 cell line was studied using MTT assay.

Example 11

In Vitro Anti-Cancer Studies

Figure 12A:
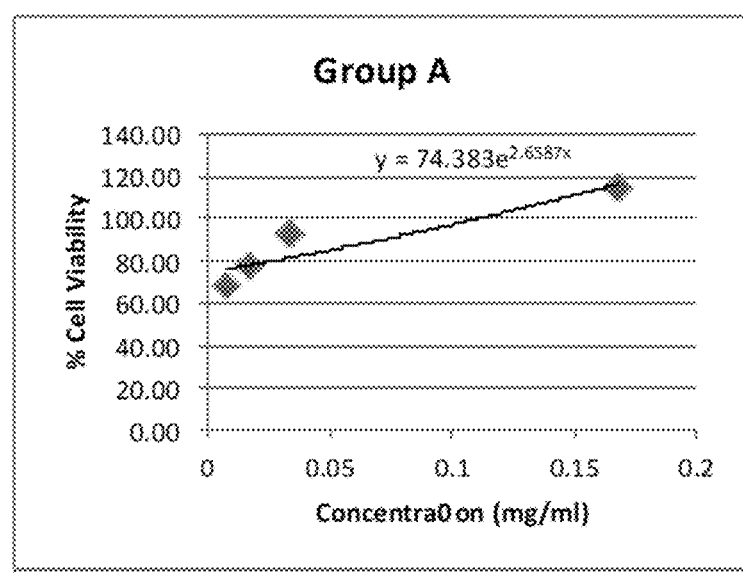
FIG. 12A is a graph showing MCF-7 cell viability percentage under different concentrations of $CuFe_2O_4$ (group A).
Figure 12B:
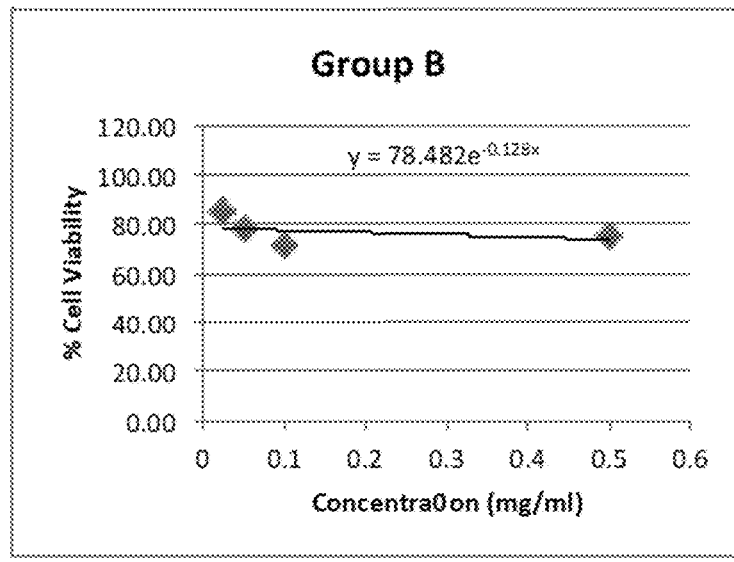
FIG. 12B is a graph showing MCF-7 cell viability percentage under different concentrations of mesoporous silica nanoparticles (group B).
Figure 12C:
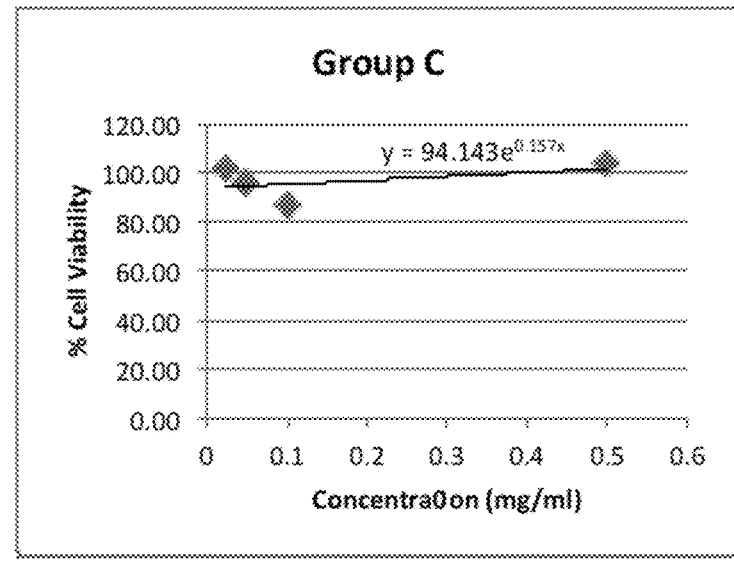
FIG. 12C is a graph showing MCF-7 cell viability percentage under different concentrations of nanoformulation containing $CuFe_2O_4$ (group C).
Figure 12D:
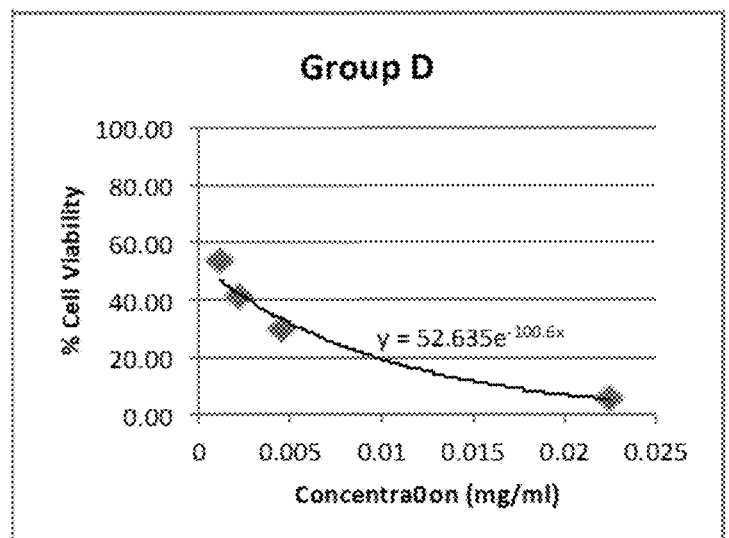
FIG. 12D is a graph showing MCF-7 cell viability percentage under different concentrations of cisplatin (group D).
Figure 12E:
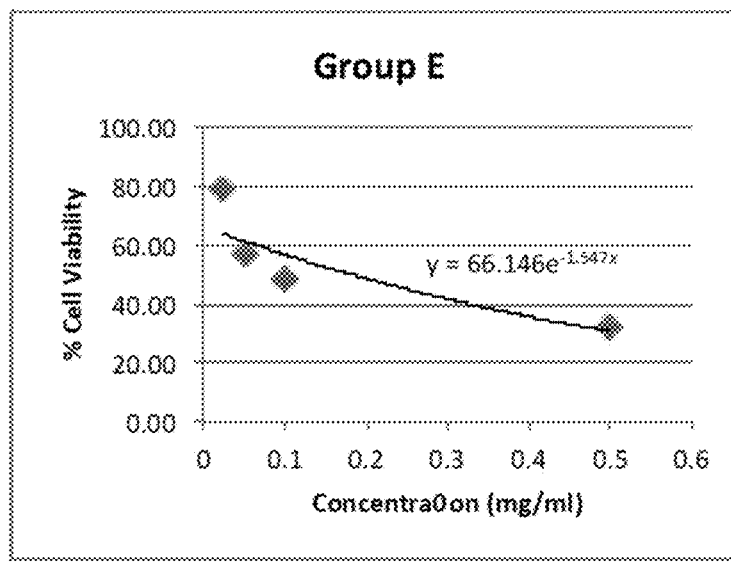
FIG. 12E is a graph showing MCF-7 cell viability percentage under different concentrations of nanotherapeutic containing $CuFe_2O_4$ (group E).
Figures 12F, 12G:
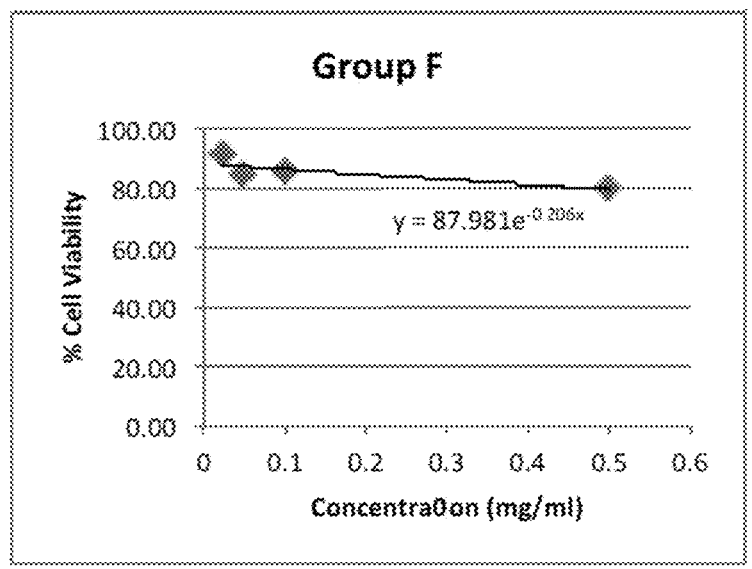
FIG. 12F is a graph showing MCF-7 cell viability percentage under different concentrations of nanotherapeutic containing $CuFe_2O_4$ and chitosan (group F).
FIG. 12G is a table summarizing $EC_{50}$ values of $CuFe_2O_4$ (group A), mesoporous silica nanoparticles (group B), nanoformulation containing $CuFe_2O_4$ (group C), cisplatin (group D), nanotherapeutic containing $CuFe_2O_4$ (group E), and nanotherapeutic containing $CuFe_2O_4$ and chitosan (group F), respectively, against MCF-7 cell lines.

To investigate cytotoxic efficiency of cisplatin-loaded/$CuFe_2O_4$-coated silica nanoparticles, cell viability using the MTT assay were assessed. Healthy cells are able to reduce MTT to the purple-colored formazan, while unhealthy/dead cells cannot. MCF7 cells were treated with the following conditions: group A ($CuFe_2O_4$), group B (silica nanoparticles), group C (silica+$CuFe_2O_4$), group D (cisplatin), group E (cisplatin+silica+$CuFe_2O_4$), and group F (cisplatin+silica+$CuFe_2O_4$+chitosan) for 48 h (FIGS. 11 and 12A-G). $CuFe_2O_4$, silica, and their combination (groups A, B, and C) did not have a significant effect on cell viability. As expected, the pure cisplatin group (D) had a significant reduction in cell viability, which reached 53.8% at the lowest concentrations used. Cisplatin was able to maintain a steady reduction in cell viability as its concentration increased. Interestingly, when cisplatin was loaded into $CuFe_2O_4$-coated silica nanoparticles (group E), a significant reduction in cell viability was observed as well. Similar to group D, group E showed a dose dependent reduction in cell viability that reached 56.5%, 48.1%, and 31.4% at 0.05, 0.1, and 0.5 mg/mL, respectively. However, the chitosan-coated nanoparticles did not have any significant reduction in cell viability. The half maximal effective concentration ($EC_{50}$) was calculated from the line equation of each condition (FIG. 12G). These results show that the cisplatin-loaded/$CuFe_2O_4$-coated silica nanoparticles can effectively reduce the viability of human breast cancer cell line MCF7, thus making it a promising option for drug delivery.

Cells were treated with the following conditions for 48 hours: group A ($CuFe_2O_4$), group B (silica nanoparticles), group C (silica+$CuFe_2O_4$), group D (cisplatin), group E (cisplatin+silica+$CuFe_2O_4$), and group F (cisplatin+silica+$CuFe_2O_4$+chitosan). For groups B, C, E, and F, treatment concentrations were as follows: 0.025, 0.05, 0.1, and 0.5 mg/ml. To accurately reflect the concentration of $CuFe_2O_4$ (group A), and cisplatin (group D) that is encapsulated within these nanoparticles, the drug loading experiments were used to calculate the actual concentration of each in the other groups. Therefore, treatment concentrations used in this experiment for group A were as follows: 0.0084, 0.0168, 0.0336, and 0.168 mg/ml. Treatment concentrations used in this experiment for group D were as follows: 0.001125, 0.00225, 0.0045, 0.0225 mg/ml. n=4 independent experiments. Dashed line represents untreated control. Error bars±S.E.M. *$p<0.05$; $p<0.01$; *$p<0.001$; ****$p<0.0001$ versus control using two-way ANOVA with Dunnett's post hoc testing.

Here, the cytotoxic efficiency of our nanoparticles was tested on the breast cancer cell line MCF7. While $CuFe_2O_4$, silica, and their combination were not cytotoxic, the cisplatin and the cisplatin-loaded/$CuFe_2O_4$-coated silica nanoparticles significantly reduced cell viability. The cisplatin containing groups (D and E) showed a dose dependent response. The cisplatin-loaded/$CuFe_2O_4$-coated silica nanoparticles (group E) caused a reduction in viability that reached 56.5%, 48.1%, and 31.4% at 0.05, 0.1, and 0.5 mg/mL, respectively.

Phadatare et al. [M. R. Phadatare, V. M. Khot, A. B. Salunkhe, N. D. Thorat, S. H. Pawar, Studies on polyethylene glycol coating on $NiFe_2O_4$ nanoparticles for biomedical applications, Journal of Magnetism and Magnetic Materials, 324 (2012) 770-772] has reported the preparation of $NiFe_2O_4$ using combustion technique followed by polyethylene glycol coating to improve the biocompatibility. The formation of agglomerated foam like morphology was observed for $NiFe_2O_4$ with a high saturation magnetization value of 35 emug$^{-1}$. Sardrolhosseini et al. [A. R. Sardrolhosseini, M. Naseri, S. A. Rashid, Polypyrrole-chitosan/nickel-ferrite nanoparticle composite layer for detecting heavy metal ions using surface plasmon resonance technique, Optics and Laser Technology 93 (2017) 216-223] reported the preparation of $NiFe_2O_4$ nanoparticle composite involving polypyrrole chitosan through electrochemical polymerization technique. In the present disclosure, efforts were made toward increasing the biocompatibility of 30 wt % CuFe2O4/HYPS by wrapping with chitosan. However, $EC_{50}$ value of F shows that wrapping cisplatin/30 wt % CuFe2O4/HYPS composite with chitosan (Group F) showed no significant effect on cell viability compared with Group D and E. Initially, the cisplatin (mmol) per gram of $CuFe_2O_4$/HYPS nanosupport was maintained at 0.15. During chitosan wrapping process, the initial pH of the chitosan solution was maintained at 2.77, which then increased to 6.4 by dropwise addition of 1 M NaOH solution. After pH adjustment, 1 g cisplatin loaded $CuFe_2O_4$/HYPS was added and the mixture was kept under stirring for 24 hours, then the pH was increased to 7. The mixture was kept under stirring for another 24 hours, then centrifuged, washed and dried under vacuum for 48 h at 37° C. The analysis of filtered solution showed a decrease in the mmol cisplatin/gram of $CuFe_2O_4$/HYPS from 0.15 to 0.03. This shows that cisplatin during chitosan pH adjustment step from 6.4 to 7 prematurely release cisplatin to the solution and therefore Group F showed less inhibitory effect compared to Group D and Group E. However, the present disclosure shows that Group E itself is the best nanoformulation that can be further tuned for chitosan loading by adjusting the cisplatin loading step after chitosan wrapping. In this way, the cisplatin release during chitosan pH adsorption process can be negated, while biocompatible of the nanocomposite will be increased. These results show that cisplatin-loaded/$CuFe_2O_4$-coated silica nanoparticles can effectively target cancerous cells. It also shows that $CuFe_2O_4$-coated silica nanoparticles could be a useful drug delivery system.

Figure 13:
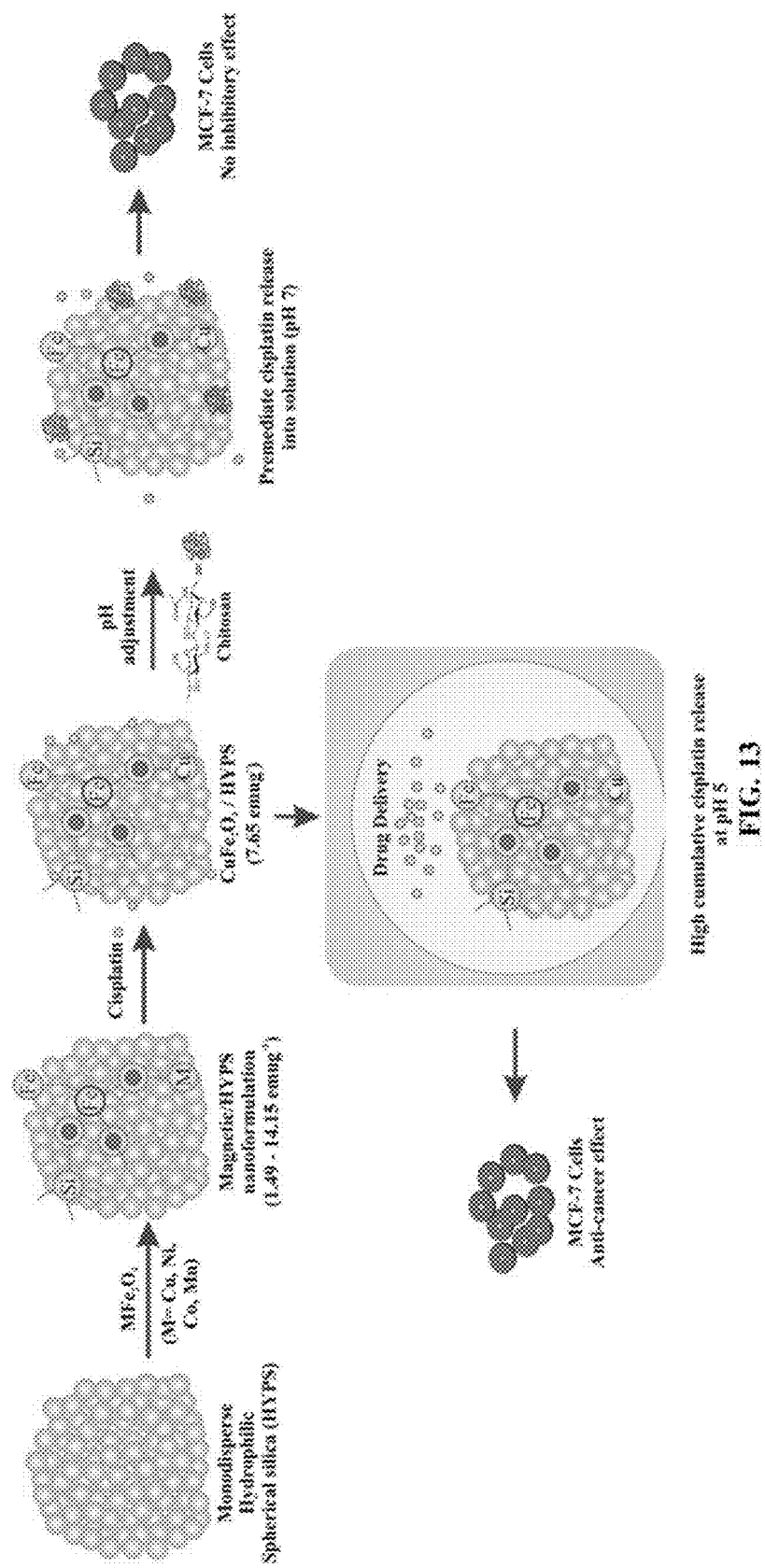
FIG. 13 is a schematic representation of drug delivery mechanism of nanotherapeutic containing $CuFe_2O_4$.

Overall, spinel ferrite/HYPS hybrid nanoformulations (FIG. 13) were explored to load the multifunctional magnetic silica drug delivery vehicle with deliverable cisplatin drug. 30% of different spinel $MFe_2O_4$ (M=Cu, Ni, Co, and Mn) has been loaded over HYPS through dry impregnation technique. The presence of cubic spinel containing tetrahedral and octahedral crystalline sites was confirmed through XRD (FIG. 1), FT-IR (FIG. 6), and DR UV-vis analysis (FIG. 10). The isotherm patterns of HYPS show that after spinel impregnation, a non-significant surface occupation (about 28%) occurs, leaving space for effective functionalization of cisplatin and chitosan wrapping. The cumulative pore volume showed about 50% occupation compared to HYPS (FIG. 4B). EDX-mapping analysis showed the presence of homogeneous silica particles, with uniform distribution of Cu and Fe mixed oxide phase of copper ferrite over HYPS silica (FIGS. 5E, 5F). VSM analysis of 30 wt % $CuFe_2O_4$/HYPS showed paramagnetic behavior, while cobalt ferrite/silica showed ferromagnetism (FIG. 7). The drug release profile of various spinel ferrite-based systems showed 30 wt % $CuFe_2O_4$/HYPS having the highest percentage cumulative cisplatin release of 90% for 72 h (FIGS. 8 and 9). Such high cisplatin release may be due to the presence of tetrahedral coordinated Pt nanoclusters, and octahedral coordinated Pt species (FIG. 10). $IC_{50}$ value of experimental design in in vitro study and percentage cell viability using MTT assay on MCF-7 cell line showed significant inhibitory effect of developed cisplatin/30 wt % $CuFe_2O_4$/HYPS nanocomposite, while development of chitosan wrapping step might be vital to further increase the biocompatibility (FIGS. 11 and 12A-G).

Example 12

An effective multifunctional spinel ferrite/silica nanocomposite system has been developed through dry impregnation technique. Among different spinel materials $MFe_2O_4$ (M=Cu, Ni, Co, and Mn), $CuFe_2O_4$/HYPS nanocomposite showed high cisplatin delivery and anticancer efficacy due to synergetic interactions between Pt and $CuFe_2O_4$. The presence of cubic copper ferrite was confirmed with uniform distribution of Cu and Fe mixed oxide phase over HYPS. The order of cisplatin drug release was in the following order: 30 wt % $CuFe_2O_4$/HYPS>30 wt % $NiFe_2O_4$/HYPS>30 wt % $MnFe_2O_4$/HYPS 30 wt % $CoFe_2O_4$/HYPS.

The low-cost spinel ferrites in presence of spherical silica have shown superior magnetic behavior, reduced aggregation and toxicity. The presence of proper surface area of HYPS helps generating magnetically active species and facilitates efficient cisplatin loading-release capabilities with targeted anticancer efficiency against cancer cell line MCF-7 in vitro.

Treatment of MCF-7 cancerous cell line with cisplatin/30 wt % $CuFe_2O_4$/HYPS (Group-E) showed high cell killing activity compared to 30 wt % $CuFe_2O_4$/HYPS-chitosan (Group-F). Overall, superparamagnetic copper ferrite/HYPS is a potential candidate for multifunctional theranostic applications for treating deadly diseases. The nanoformulation with magnetic property of spinel loaded over monodisperse silica can be further manipulated with drugs, antioxidants, and biocompatible polymers.

The invention claimed is:

1. A nanotherapeutic, comprising:
a nanoformulation, comprising:
mesoporous silica nanoparticles in the form of monodispersed spherical silica having a particle size distribution of about 80 nm; and
spinel ferrite nanoclusters of formula (I)

$$MFe_2O_4 \tag{I}$$

wherein M is at least one transition metal element selected from the group consisting of Cu and Ni;
wherein:
the spinel ferrite nanoclusters are impregnated on the mesoporous silica nanoparticles; and
the spinel ferrite nanoclusters are present in an amount of 25-35 wt % relative to a total weight of the nanoformulation, and
cisplatin encapsulated within pores of the nanoformulation,
wherein the nanoformulation has a cisplatin release at a pH 5 at 37° C. for 72 h of 60-80 wt. % and wherein the pores of the nanoformulation have a pore diameter in a range of 10-25 nm, and the nanoformulation has a pore volume in a range of 0.05 0.3 $cm^3$/g, a BET surface area in a range of 15-70 $m^2$/g, and a saturation magnetization value in a range of 7-15 emu/g.

2. The nanotherapeutic of claim 1, wherein the cisplatin is present at a concentration of 0.01-10 mmol/g relative to a total weight of the nanoformulation.

3. The nanotherapeutic of claim 1, further comprising one or more pharmaceutically acceptable carriers and/or excipients selected from the group consisting of a buffer, an inorganic salt, a fatty acid, a vegetable oil, a synthetic fatty ester, a surfactant, and a polymer.

4. The nanotherapeutic of claim 1, wherein the spinel ferrite nanoclusters are paramagnetic.

* * * * *